US008580975B2

(12) United States Patent
Ghosh et al.

(10) Patent No.: US 8,580,975 B2
(45) Date of Patent: Nov. 12, 2013

(54) SYNTHESIS OF MACROCYCLIC CANCER CHEMOTHERAPY AGENTS AND METHODS OF USE

(75) Inventors: Arun K Ghosh, West Lafayette, IN (US); Xiaoming Xu, Dallas, TX (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 12/812,067

(22) PCT Filed: Jan. 9, 2009

(86) PCT No.: PCT/US2009/030597
§ 371 (c)(1),
(2), (4) Date: Oct. 18, 2010

(87) PCT Pub. No.: WO2009/089450
PCT Pub. Date: Jul. 16, 2009

(65) Prior Publication Data
US 2011/0028540 A1 Feb. 3, 2011

Related U.S. Application Data

(60) Provisional application No. 61/020,498, filed on Jan. 11, 2008.

(51) Int. Cl.
*C07D 335/04* (2006.01)
(52) U.S. Cl.
USPC ............................................................ 549/23
(58) Field of Classification Search
USPC ............................................................ 549/23
See application file for complete search history.

(56) References Cited

U.S. PATENT DOCUMENTS

2007/0287745 A1  12/2007 Gallagher et al.

FOREIGN PATENT DOCUMENTS

WO    WO 00/58254       10/2000
WO    WO 2009/112077     9/2009

OTHER PUBLICATIONS

Mandal et al., J. Org. Chem. 1998, 63, 1901-1905). Likewise, see.*
Vedejs et al., J. Org. Chem. 1993,58, 30463050).*
Knight et al., J. Am. Chem. Soc. 115 (20): 9293-9294.*
Venkatesh et al., J. Pharm. Sci. 89, 145-54 (2000) (p. 146, left column).*
Dorwald F. A. Side Reactions in Organic Synthesis, 2005, Wiley: VCH, Weinheim p. IX of Preface p. 1-15.*
International Search Report/Written Opinion completed Feb. 2, 2009 for PCT/US2009/030597.
Denissova, Irina, et al., "Stereoselective Formation of Quaternary Carbon Centers and Related Functions", 2003, Tetrahedron, No. 59, pp. 10105-10146.
Ghosh, Arun K., et al., Synthetic Studies of Microtubule Stabilizing Agent Peloruside A: an Asymmetric Synthesis of C10-C24 Segment, Tetrahedron Letters, 2003, 44, 7659-7661.
Bertinato, Peter, Erik J. Sorensen, Dongfang Meng, and Samuel J. Danishefsky, "Studies toward a Synthesis of Epothilone A: Stereocontrolled Assembly of the Acyl Region and Models for Macrocyclization," J. Org. Chem. 1996, 61, 8000-8001.
Evans, David A., Percy H. Carter, Erick M. Carreira, Andre B. Charette, Joelle A. Prunet, and Mark Lautens, "Total Synthesis of Bryostatin 2," J. Am. Chem. Soc. 1999, 121, 7540-7552.
Ghosh, A. K.; Kin, J.-H.; "An Enantioselective Synthesis of the $C_{1-C9}$ Segment of Antitumor Macrolide Peloruside A," Tetrahedron Letters 2003, 44, 3967-3969.
Jin, M.; Taylor, R. E., "Total Synthesis of (+)-Peloruside A," Org. Lett. 2005, vol. 7, No, 7, 1303-1305.
Kagawa, Natsuko, Masataka Ihara, and Masahiro Toyota, "Total Synthesis of (+)-Mycalamide A," Organic Letters, 2006, vol. 8, No. 5, 875-878.
Keck, Gary E, Dennie S. Welch and Yam B. Poudel, "Synthetic studies toward bryostatin 1:, preparation of a $C_1$-$C_{16}$ fragment by pyran annulation," Science Direct, Tetrahedron Letters 47 (2006) 8267-8270.
Keck, Gary E. and Anh P. Truong, "Synthetic Studies on the Bryostatins: Preparation of a Truncated BC-Ring Intermediate by Pyran Annulation," Organic Letters, 2005, vol. 7, No. 11, 2149-2152.
Liao, X.; Wu, Y.; De Brabander, J. K., "Total Synthesis and Absolute Configuration of the Novel Microtubule-Stabilizing Agent Peloruside A," Angew Chem Int Ed 2003, 42, 1648-1652.
Liu, B.; Zhou, W.-S.; "Toward the Total Synthesis of Natural Peloruside A: Stereoselective Synthesis of the Backbone of the Core," Org Lett. 2004, vol. 6, No. 1, 71-74.
Paterson, I.; Di Francesco, M. E.; Kuhn, T. "Toward the Synthesis of Peloruside A: Fragment Synthesis and Coupling Studies," Org Lett. 2003, vol. 5, No. 4, 599-602.
Roush, William R. and Lance A. Pfeifer, "Stereoselective N-Acylation Reactions of α-Alkoxy Carbamates," J. Org. Chem. 1998, 63, 2062-2063.
Roush, William R., and Lance A. Pfeifer, "Total Synthesis of Mycalamide A and 7-epi-Mycalamide A," Organic Letters, 2000, vol. 2, No. 6, 859-862.
Sinha, Subhash C.,Carlos F. Barbas III and Richard A. Lerner "The antibody catalysis route to the total synthesis of epothilones," Proc. Natl. Acad. Sci. USA, vol. 95, pp. 14603-14608, Dec. 1998.
Taylor, Richard E. and Jin, Meizhong, "Toward a Total Synthesis of Peloruside A: Enantioselective Preparation of the C8-C19 Region," Organic Letters, 2003, vol. 5, No. 26, 4959-4961.

*Primary Examiner* — Nizal Chandrakumar
(74) *Attorney, Agent, or Firm* — Barnes & Thornburg LLP

(57) ABSTRACT

Herein are described a process for forming a quaternary carbon useful in the preparation of macrolactones, an enantioselective synthesis of (+)-peloruside A, and methods for treating a patient in need of relief from cancer or a cancer-related disease. The described processes are useful for preparing compounds containing quaternary carbons, including structural analogs and derivatives of peloruside A.

23 Claims, No Drawings

(56) References Cited

OTHER PUBLICATIONS

Wender, Paul A., and Adam J. Schrier. "Total Synthesis of Bryostatin 9," J. Am. Chem. Soc. 2011, 133, 9228-9231.

Yang, Zhen, Yun He, Dionisios Vourloumis, Hans Vallberg, and K. C. Nicolaou "Total Synthesis of Epothilone A: The Olefin Metathesis Approach," Angew. Chem. Inr. Ed. Engl. 1997, 36. No. 112, 166-168.

* cited by examiner

SYNTHESIS OF MACROCYCLIC CANCER CHEMOTHERAPY AGENTS AND METHODS OF USE

GOVERNMENT RIGHTS

This invention was made with Government support under Grant No. NIGMS 53386, awarded by the National Cancer Institute and the National Institutes of Health. The Government has certain rights in the invention.

CROSS-REFERENCE TO RELATED APPLICATIONS

This application is a U.S. national application under 35 U.S.C. §371(b) of International Application Serial No. PCT/US2009/030597 filed Jan. 9, 2009, which claims priority under 35 USC §119(e) to U.S. Provisional Application Ser. No. 61/020,498, filed Jan. 11, 2008, the disclosure of which is incorporated herein by reference

BACKGROUND AND SUMMARY

Peloruside A (1), a 16-membered macrolide antitumor agent was first isolated by West and Northcote from the New Zealand marine sponge, *Mycale hentscheli* (West, L. M.; Northcote, P. T.; Battershill, C. N. J Org Chem 2000, 65, 445). It has shown potent antitumor activity against P388 murine leukemia cells with an $IC_{50}$ value of 10 ng/mL. Peloruside A is a microtubule stabilizing agent and arrests cells in the G2-M phase (Hood, K. A.; West, L. M.; Rouwe, B.; Northcote, P. T.; Berridge, M. V.; Wakefield, S. J.; Miller, J. H. Cancer Res 2002, 62, 3356). However, like laulimalide, peloruside A binds to the non-taxoid site of tubulin and has shown to a synergistic effect with taxol (Pryor, D. E.; O'Brate, A.; Bilcer, G.; Diaz, J. F.; Wang, Y.; Wang, Y.; Kabaki, M.; Jung, M. K.; Andreu, J. M.; Ghosh, A. K.; Giannakakou, P.; Hamel, E. Biochemistry 2002, 41, 9109). The intriguing structure, very low natural abundance and important biology of peloruside A attracted immense interest in synthesis ((a) Paterson, I.; Di Francesco, M. E.; Kuhn, T. Org. Lett. 2003, 5, 599; (b) Ghosh, A. K.; Kim, J.-H. Tetrahedron Letters 2003, 44, 3967; (c) Ghosh, A. K.; Kim, J.-H. Tetrahedron Letters 2003, 44, 7659; (d) Liu, B.; Zhou, W. S. Org. Lett. 2004, 6, 71). Thus far, De Brabander et al. and subsequently Taylor and co-workers have achieved the total synthesis of peloruside A ((a) Liao, X.; Wu, Y.; De Brabander, J. K. Angew Chem Int Ed Engl 2003, 42, 1648; (b) Jin, M.; Taylor, R. E. Org. Lett. 2005, 7, 1303). Even so, additional synthetic procedures are useful to ensure the supply of peloruside A, and also to provide a route to analogs and derivatives of this important molecule.

Described herein is a process for forming a quaternary carbon, the process comprising the steps of; reacting a compound containing a 2-alkyl-2-ene-1-one moiety with a source of nucleophilic hydride; and adding a compound containing an aldehyde to form the quaternary carbon. The process may be used to prepare a wide variety of chemical compounds. In one illustrative embodiment, the process may be used for the preparation of a macrolactone such as, but not limited to, a peloruside, a mycalamide, a bryostatin, an epothilone, and the like.

Also described herein is a process for preparing a peloruside, including peloruside A and analogs and derivatives thereof. The process comprises the step of preparing an aldol intermediate that is subsequently converted into the peloruside. The compounds described herein are useful for treating a patient in need of relief from cancer, a cancer-related disease, or a disease linked to the presence of a population of pathogenic cells.

DETAILED DESCRIPTION

As shown below, described herein is a synthetic process that includes the assembly of fragments I and II by a stereoselective aldol reaction, followed by a macrolactonization of the corresponding carboxylic acid at C-1 and hydroxyl group at C-16. Without being bound by theory, it is believed that the presence of the gem-dimethyl group at C-10, makes the C-7 to C-11 lactol segment of peloruside A sterically very hindered. It has been reported that aldol reactions involving gem-dimethyl ketone and aldehyde often result in poor yield and side reactions, as described by Liu, B.; Zhou, W. S. Org. Lett. 2004, 6, 71. The foregoing citation, along with all other citations disclosed herein, are incorporated herein by reference. Both published peloruside A syntheses utilized methyl ketone aldol reactions to avoid this reported problem ((a) Liao, et al, 2003; Jin, et al, 2005). In contrast, it has been discovered herein that the process described herein provides for the installation of the C-10 gem-dimethyl and C-11 hydroxyl group by an efficient reductive enolization of enone II followed by reaction with aldehyde I.

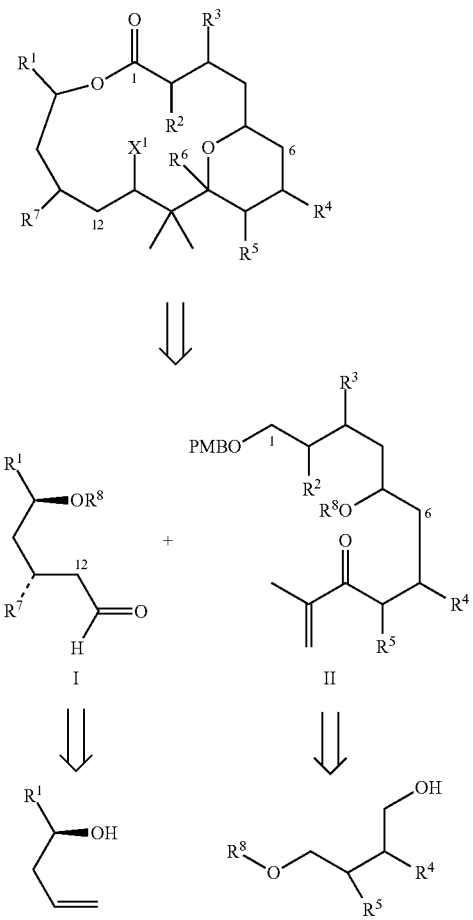

Retrosynthetic Route of the Processes Described Herein

In one embodiment, a process for forming a quaternary carbon is described, the process comprises the steps of (a)

reacting a compound containing a 2-alkyl-2-ene-1-one moiety with a source of nucleophilic hydride; and (b) adding a second compound containing an aldehyde to form the quaternary carbon.

In another embodiment, the process of forming a compound wherein the compound contains a quaternary carbon is described, where the process comprises the steps of (a) reacting a compound containing a 2-alkyl-2-ene-1-one moiety with a source of nucleophilic hydride; and (b) adding a second compound containing an aldehyde to form the quaternary carbon.

In another embodiment, the processes described above wherein the compound containing a quaternary carbon is a macrolactone are described.

In another embodiment, any of the processes described above wherein the macrolactone is a bryostatin, a peloruside, a mycalamide or an epothilone are described.

In another embodiment, any of the processes described above wherein the macrolactone modulates microtubule assembly are described.

In another embodiment, any of the processes described above wherein the macrolactone has the formula

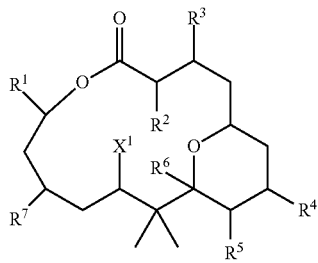

wherein:
R¹ is

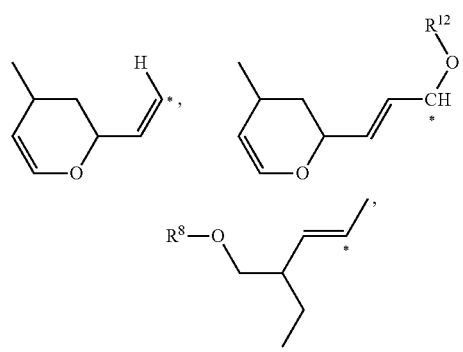

where * shows the point of attachment and R8 and R12 are independently hydrogen, alkyl, heteroalkyl, arylalkyl, heteroarylalkyl, or an oxygen protecting group;

$R^2$, $R^3$, $R^4$, $R^5$, $R^6$ and $R^7$ are each independently selected from the group consisting of hydrogen, alkyl, hydroxy, and alkoxy; and $X^1$ is hydrogen, hydroxy, alkoxy or together with the carbon to which it is attached forms a carbonyl or an oxime are described.

In another embodiment, any of the processes described above wherein the macrolactone has the formula

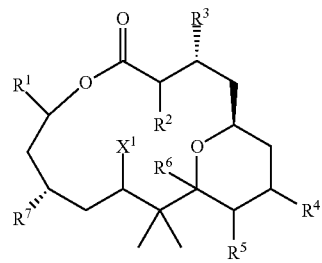

wherein:
R¹ is

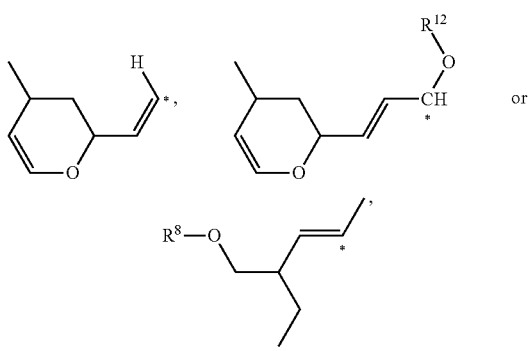

where * shows the point of attachment;

$R^2$, $R^3$, $R^4$, $R^5$, $R^6$ and $R^7$ are each independently selected from the group consisting of hydrogen, alkyl, hydroxy, and alkoxy; $X^1$ is hydrogen, hydroxy, alkyl, alkoxy or together with the carbon to which it is attached forms a carbonyl or an oxime; and $R^8$ and $R^{12}$ are independently hydrogen, alkyl, heteroalkyl, arylalkyl, heteroarylalkyl, or an oxygen protecting group are described.

In another embodiment, any of the processes described above wherein the macrolactone has the formula

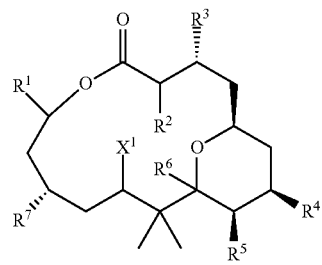

wherein
R¹ is

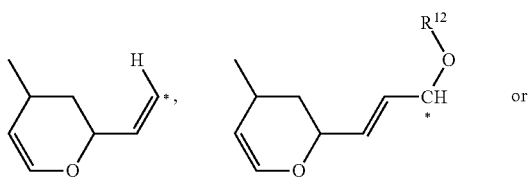

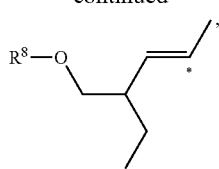

where * shows the point of attachment;

$R^2, R^3, R^4, R^5, R^6$ and $R^7$ are each independently selected from the group consisting of hydrogen, alkyl, hydroxy, and alkoxy; $X^1$ is hydrogen, hydroxy, alkyl, alkoxy or together with the carbon to which it is attached forms a carbonyl or an oxime; and $R^8$ and $R^{12}$ are independently hydrogen, alkyl, heteroalkyl, arylalkyl, heteroarylalkyl, or an oxygen protecting group are described.

In another embodiment, any of the processes described above wherein $R^3$ is methoxy and $R^7$ is methoxy are described.

In another embodiment, any of the processes described above wherein $R^6$ is hydrogen is described. In another embodiment, any of the processes described above wherein $R^2$ is hydrogen are described.

In another embodiment, any of the processes described above wherein $R^2$ is hydroxy; $R^4$ is methoxy; $R^5$ is hydroxy; $R^6$ is hydroxy; $X^1$ is hydroxy; and
$R^1$ is

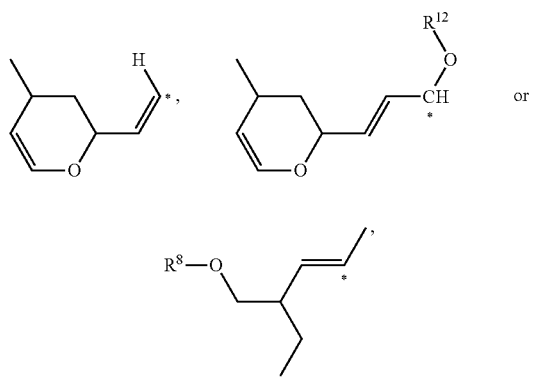

where * shows the point of attachment and $R^8$ and $R^{12}$ are independently hydrogen, alkyl, heteroalkyl, arylalkyl, heteroarylalkyl, or an oxygen protecting group are described.

In another embodiment, any of the processes described above wherein $R^2$ is hydroxy; $R^4$ is methoxy; $R^5$ is hydroxy; $R^6$ is hydrogen, hydroxy, alkyl, such as methyl or ethyl, and the like, or alkoxy, such as methoxy or ethoxy, and the like; $X^1$ is hydroxy; and $R^1$ is 4-(R)-hydroxymethyl-hex-2-(Z)-ene-2-yl are described.

In another embodiment, any of the processes described above wherein $R^2$ is hydroxy; $R^4$ is methoxy; $R^5$ is hydroxy; $R^6$ is hydroxy; $X^1$ is hydrogen, or epi-hydroxy, alkoxy, such as methoxy or ethoxy, and the like, or alkyl, such as methyl or ethyl, and the like or $X^1$ and the attached carbon form a carbonyl; and $R^1$ is 4-(R)-hydroxymethyl-hex-2-(Z)-ene-2-yl are described.

In another embodiment, any of the processes described above wherein $R^2$ is hydrogen, hydroxy, or alkyl, such as methyl or ethyl, and the like; $R^4$ is methoxy; $R^5$ is hydroxy; $R^6$ is hydroxy; $X^1$ is hydroxy; and $R^1$ is 4-(R)-hydroxymethyl-hex-2-(Z)-ene-2-yl are described.

In another embodiment, any of the processes described above wherein $R^2$ is hydroxy; $R^4$ is hydrogen, hydroxy, alkoxy, such as methoxy or ethoxy, and the like, or alkyl, such as methyl or ethyl, and the like; $R^5$ is hydroxy; $R^6$ is hydroxy; $X^1$ is hydroxy; and $R^1$ is 4-(R)-hydroxymethyl-hex-2-(Z)-ene-2-yl are described.

In another embodiment, any of the processes described above wherein $R^2$ is hydroxy; $R^4$ is methoxy; $R^5$ is hydrogen, hydroxy, alkoxy, such as methoxy or ethoxy, and the like, or alkyl, such as methyl or ethyl, and the like; $R^6$ is hydroxy; $X^1$ is hydroxy; and $R^1$ is 4-(R)-hydroxymethyl-hex-2-(Z)-ene-2-yl are described.

In another embodiment, any of the processes described above wherein the source of nucleophilic hydride is lithium (sec-butyl)$_3$borohydride are described.

In one embodiment analogs of peloruside may be prepared by the processes described herein.

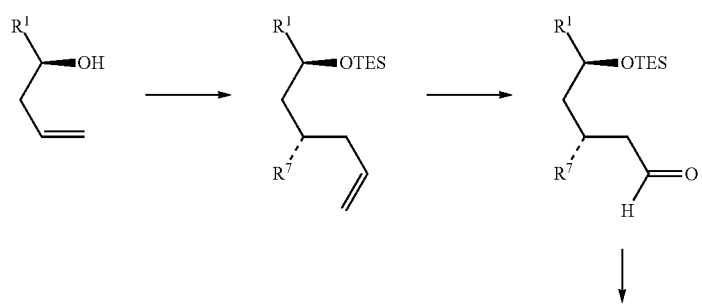

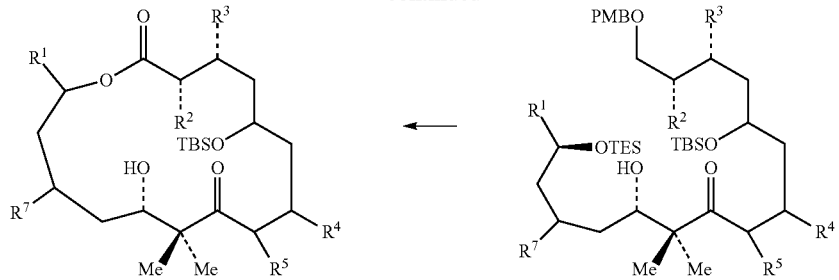

In another aspect, the C7 and C8 hydroxyl groups in 2 may provided by asymmetric dihydroxylation while the C5 center may be setup by Brown allylation (Jadhav, P. K.; Bhat, K. S.; Perumal, P. T.; Brown, H. C. J. Org. Chem. 1986, 51, 432) and the C2 and C3 chiral centers may be derived from known compound 4. Aldehyde 3 may be obtained from asymmetric allylation of the corresponding aldehyde derived from known compound 5 (Ghosh, A. K.; Kim, J.-H. Tetrahedron Letters 2003, 44, 7659).

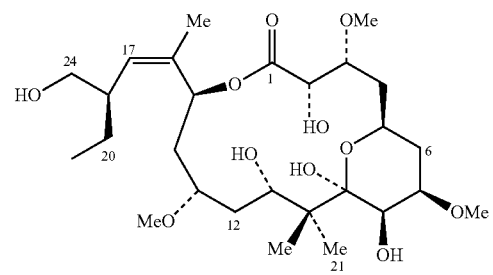

Peloruside A (1)

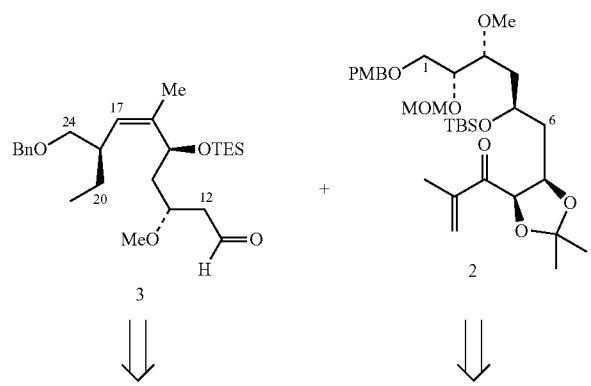

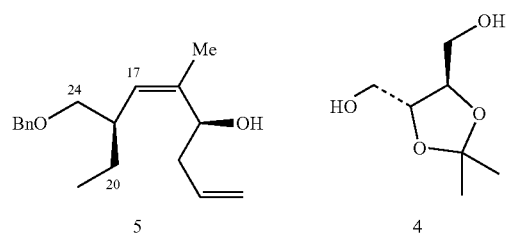

-continued
Scheme 1

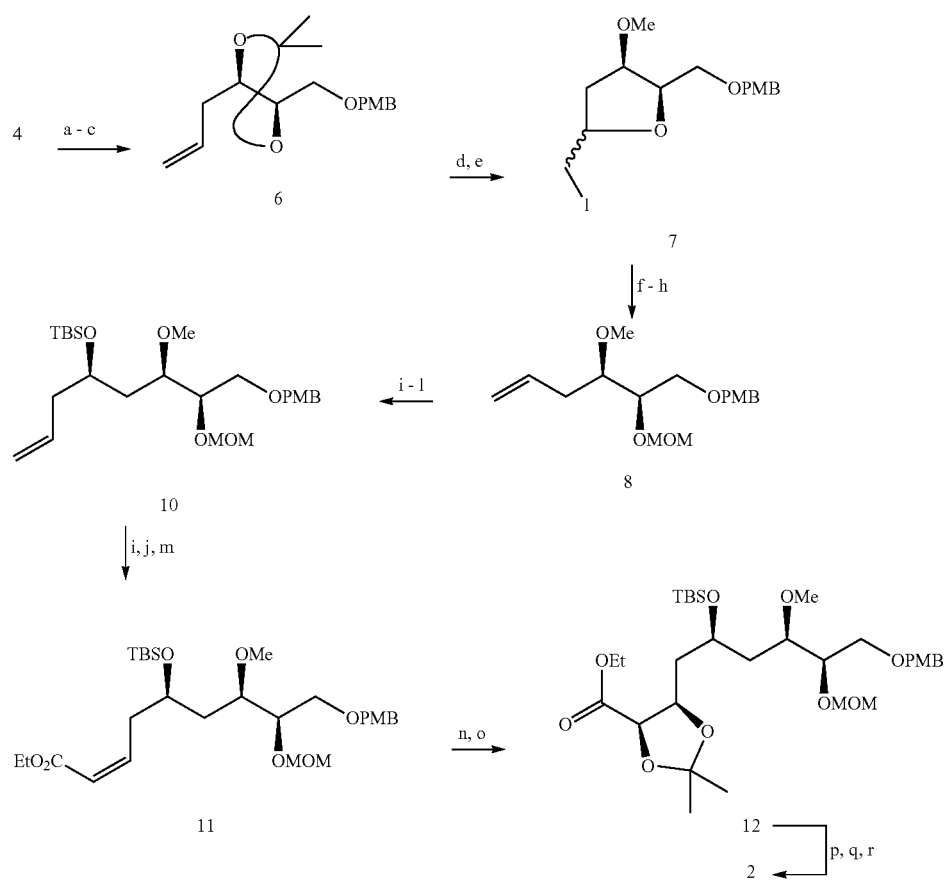

Conditions: (a) NaH, PMBCl, 23° C. 78%; (b) Ph$_3$P, I$_2$, Imidazole, 0° C., 88%; (c) CH$_2$=CHMgBr, CuI, HMPA, −30° C. to 0° C., 85%; (d) 10% HCl, MeOH, 23° C.; (e) CH$_3$CN, NaHCO$_3$, I$_2$, 0° C. to 23° C., 82% (2 steps); (f) Me$_3$O$^+$BF$_4^-$, proton sponge, 23° C., 87%; (g) 95% EtOH, Zn; (h) MOMCl, DIPEA, 23° C., 88% (2 steps); (i) NMO, OsO$_4$, Acetone/H$_2$O, 0° C.; (j) NaIO$_4$, THF/H$_2$O, 23° C.; (k) (+)-Ipc$_2$BOMe, CH$_2$=CHCH$_2$MgBr, 23° C., aldehyde, −78° C., 2 h, NaOH, H$_2$O$_2$, 77% (3 steps); (l) TBSCl, imidazole, DMAP, 96%; (m) (o-cresol)$_2$P(O)CH$_2$CO$_2$Et, NaH, NaI, 0° C., aldehyde, −78° C. to −50° C., 89% (3 steps); (n) AD-mix-α, CH$_3$SO$_2$NH$_2$, $^t$BuOH—H$_2$O, 0° C., 72 h, 97%; (o) CH$_2$=C(OMe)Me, PPTS, 94%; (p) Dibal-, −78° C., 96%; (q) CH$_2$=C(Me)MgBr, THF, 0° C., 86%; (r) Dess-Martin, 23° C., 90%.

One illustrative embodiment of the processes described herein is shown in Scheme 1. The synthesis of C1-C11 segment 2 commences with the commercially available (−)-2,3-O-isopropylidene-D-threitol 4. It is converted to iso-propylidene derivative 6 in a three step sequence involving; (1) mono benzylation of 4 with sodium hydride and PMBCl; (2) conversion of alcohol to iodide and (3) allylation of the resulting iodide with Grignard reagent. Acid-catalyzed removal of isopropylidene group followed by iodoetherfication with iodine in the presence of sodium bicarbonate and methylation of the C3 hydroxyl group with trimethyloxonium tetrafluoroborate (Earle, M.; Fairhurst, R.; Giles, R.; Heaney, H. Synlett 1991, 728) affords iodide 7. Reductive cleavage of the iodoether followed by protection of alcohol as its MOM ether provides 8. Conversion of the terminal olefin to aldehyde (Yu, W.; Mei, Y.; Kang, Y.; Hua, Z.; Jin, Z. Org. Lett. 2004, 6, 3217) and asymmetric allylation followed by TBS protection and furnishes 10. The terminal olefin is converted to aldehyde as described above and Horner-Emmons olefination of the resulting aldehyde furnishes the Z olefin 11 selectively (Z:E 7:1, 89% in 3 steps). Sharpless asymmetric dihydroxylation (Kolb, H. C.; VanNieuwenhze, M. S.; Sharpless, K. B. Chem. Rev. 1994, 94, 2483) of the pure Z-olefin proceeds in excellent yield (97%) and diastereoselectivity (dr 6.3:1 by 1H NMR analysis). Protection of the diol as the isopropylidene derivative yields the ester 12. Dibal-H reduction of the ester followed by addition of the Grignard reagent and subsequent Dess-Martin oxidation of the resulting alcohol accomplishes the synthesis of the enone segment 2.

The synthesis of C11-C24 segment 3 is shown in Scheme 2. Homoallylic alcohol 5 is synthesized utilizing chiral imide 13 as described previously (Ghosh, A. K.; Kim, J.-H. Tetrahedron Letters 2003, 44, 7659). The hydroxyl group is protected as its TES ether. Oxidative cleavage of the terminal olefin provides aldehyde which is exposed to asymmetric allylation (Jadhav, et al; 1986) to furnish alcohol 15 diastereoselectively (dr 5:1 by 1H NMR analysis). Alcohol 15 is converted to methyl ether as described above and oxidative cleavage of the resulting olefin provides aldehyde 3 in good yield. With the syntheses of enone 2 and aldehyde 3, our synthetic strategy calls for the assembly of these segments by reductive enolization of enone 2 followed by aldol addition to aldehyde 3. Thus, reaction of 2 with 1.1 equivalent of L-selectride at −78° C. for 10 min provides the corresponding enolate. Reaction of this enolate with aldehyde 3 at −78° C. for 1 h affords the aldol product 17 and its diastereomer, 17a, as a 4:1 mixture in 92% isolated yield. The diastereomers are readily separated by silica gel chromatography. This aldol protocol is practical and the efficiency of this process is significantly improved compared to direct aldol reaction with a related ketone enolate and aldehyde (LDA induced a-dimethyl ketone aldol coupling results in a 29% yield and 40% loss of starting material).

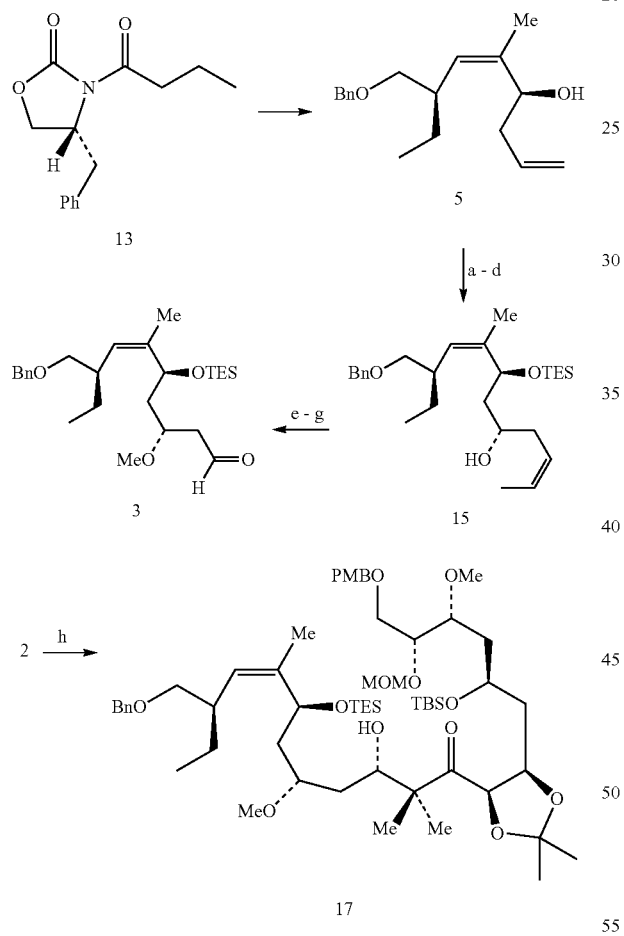

Conditions: (a) TESOTf, 2,6-lutidine, 90%; (b) NMO, OsO$_4$, Acetone/H$_2$O, 0° C.; (c) Pb(OAc)$_4$, CH$_2$Cl$_2$; (d) (−)-Ipc$_2$BOMe, Allyl magnesium bromide, 23° C., then −78° C., 2 h, NaOH, H$_2$O$_2$, 61% (3 steps); (e) Me$_3$OBF$_4$, proton sponge, 23° C., 98%; (f) NMO, OsO$_4$, Acetone/H$_2$O, 0° C.; (g) Pb(OAc)$_4$, CH$_2$Cl$_2$, 74% (2 steps); (h) L-selectride, Et$_2$O, −78° C., 10 min, then 3, −78° C., 1 h; 92%.

The subsequent elaboration to macrolactone and synthesis of peloruside A is shown in Scheme 3. The TES group of 17 is selectively removed by reaction with a catalytic amount of DDQ in aqueous THF. Subsequent exposure of resulting PMB ether to an excess of DDQ in the presence of pH 7 buffer removes the PMB group. TPAP oxidation of 18 selectively oxidizes the primary alcohol to an aldehyde, which is oxidized with sodium chlorite to the carboxylic acid. The resulting acid is subjected to Yamaguchi lactonization (Inanaga, J. H., K.; Saeki, H.; Katsuki, T. and Yamaguchi, M., Bull. Chem. Soc. Jpn. 1979, 52, 1989) protocol with 2,4,6-trichlorobenzoyl chloride in the presence of DMAP to provide the corresponding macrolactone 19 in good yield. Macrolactone 19 is converted to synthetic (+)-peloruside A as follows: deprotection of the TBS and isopropylidene groups with 1M aqueous HCl to provide a hemiketal, selective methylation of the equatorial hydroxyl group with trimethyloxonium tetrafluoroborate, removal of the benzyl group by transfer hydrogenation conditions and removal of MOM group by exposure to aqueous 4N HCl (Removal of isopropylidene group results in an equilibrium mixture of macrocycle and hemi-ketal. Final chromatographic purification is made after the final step).

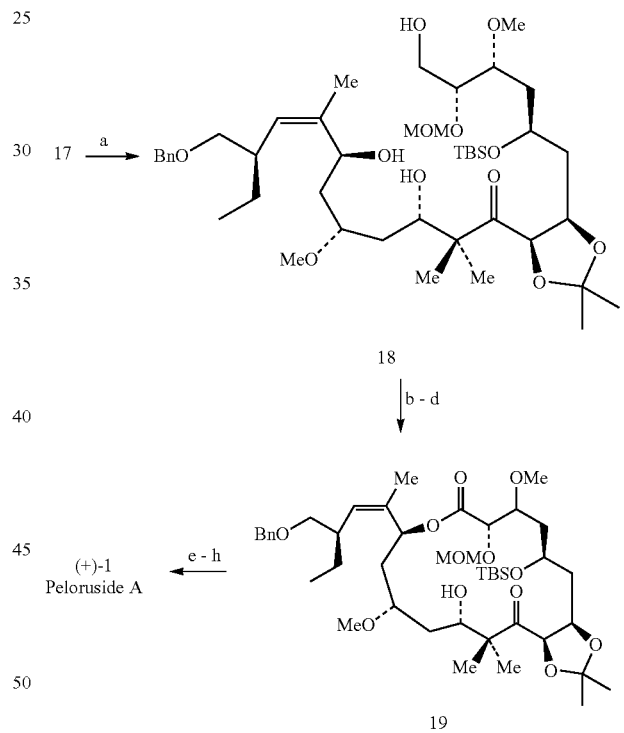

Conditions: (a) DDQ, THF/H$_2$O, 23° C., 2 h, then DDQ, CH$_2$Cl$_2$, pH 7, 5 h, 70%; (b) TPAP, NMO, CH$_2$Cl$_2$, 4 Å MS, 0° C.; (c) NaClO$_2$, NaH$_2$PO$_4$, H$_2$O, tBuOH, 2-methyl-2-butene; 23° C., 52% (2 steps) (d) 2,4,6-Cl$_3$-C$_6$H$_2$COCl, Et$_3$N, PhMe, then DMAP, PhMe, 23° C., 24 h, 64%; (e) 1M HCl, THF, 23° C., 8 h; (f) Me$_3$OBF$_4$, 2,6-di-tert-butylpyridine, 0° C.; 73% (2 steps) (g) Pd/C, HCOOH, MeOH, 23° C., 1 h; (h) 4N aq. HCl, THF, 23° C., 3.5 h; 50% (2 steps).

In the example where the compound was (+)-peloruside A, spectral data (1H and 13C NMR) of synthetic compound (1) was identical to that reported for the naturally occurring compound.

In another embodiment an intermediate compound of structure

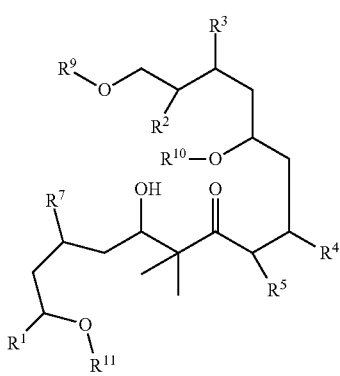

wherein $R^1$ is

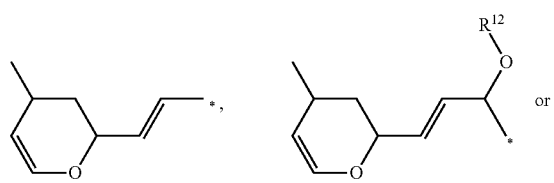

$R^2$ is hydrogen, methyl, alkyl, hydroxy or alkoxy; $R^3$ is hydrogen, methyl, ethyl, alkyl, methoxy, or alkoxy; $R^4$, $R^5$ and $R^7$ are each independently selected from the group consisting of hydrogen, methyl, ethyl, alkyl, hydroxy, methoxy and alkoxy; $R^8$ and $R^{12}$ are in each instance independently selected from the group consisting of hydrogen, alkyl, alkylaryl and oxygen protecting group; $R^9$ and $R^{10}$ are each an independently selected oxygen protecting group; which is useful for the manufacture of a compound of the structure

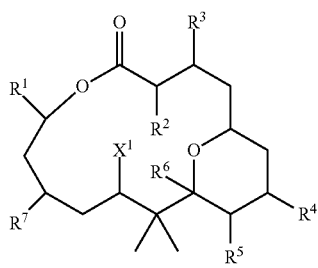

wherein:

$R^1$, $R^2$, $R^3$, $R^4$, $R^5$, and $R^7$, $R^8$, $R^9$ and $R^{10}$ are as defined above; $R^6$ is hydrogen, methyl, alkyl, hydroxy or alkoxy; $X^1$ is hydroxy, alkyl, alkoxy, or together with the carbon to which it is attached to form a carbonyl or and oxime; is synthesized by reacting a compound of structure

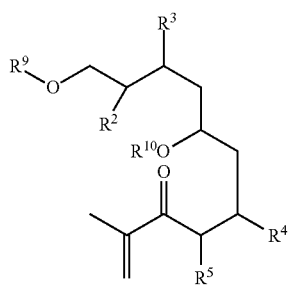

wherein $R^2$, $R^3$, $R^4$, $R^5$, $R^9$ and $R^{10}$ are as defined above; with a source of nucleophilic hydride and adding to the mixture a compound of structure

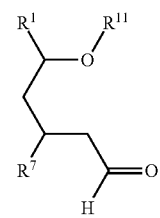

wherein; $R^1$, $R^7$ and $R^{11}$ are defined above to yield the intermediate compound.

In one embodiment compounds of the formula

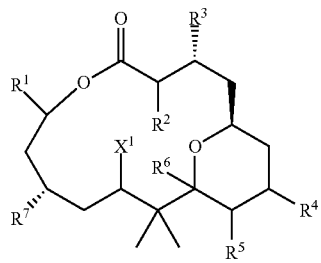

or a pharmaceutically acceptable salt thereof
wherein:
$R^1$ is

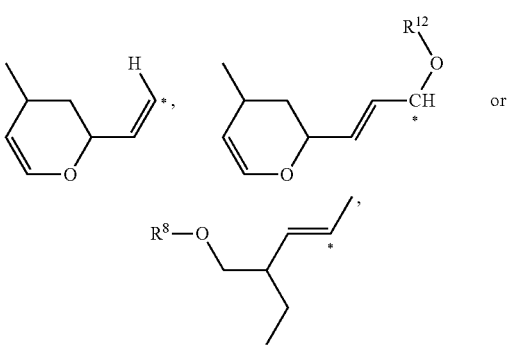

where * shows the point of attachment;

$R^2$, $R^3$, $R^4$, $R^5$, $R^6$ and $R^7$ are each independently selected from the group consisting of hydrogen, alkyl, hydroxy, and alkoxy; $X^1$ is hydrogen, hydroxy, alkoxy, alkyl or together with the carbon to which it is attached forms a carbonyl or an oxime; and $R^8$ and $R^{12}$ are independently hydrogen, alkyl, heteroalkyl, arylalkyl, heteroarylalkyl, or an oxygen protecting group;

providing that the compound is not (+)-peloruside A or (−)-peloruside A; and providing that a) when $R^2=R^6=X^1$=hydroxy and $R^3=R^4$=OMe, then $R^5$ is hydroxy; b) when $R^5=R^6=X^1$=hydroxy and $R^3=R^4$=OMe, then $R^2$ is not methoxymethoxy; and c) $R^2$ and $R^3$ are not both hydrogen are described.

In another embodiment, the compounds described in the preceding embodiment having the formula

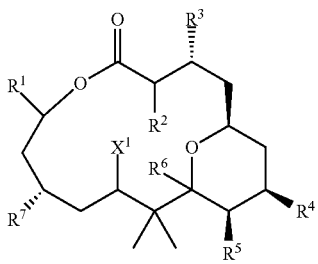

wherein
$R^1$ is

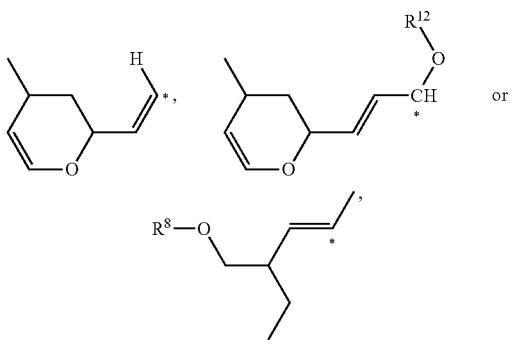

where * shows the point of attachment;

$R^2$, $R^3$, $R^4$, $R^5$, $R^6$ and $R^7$ are each independently selected from the group consisting of hydrogen, alkyl, hydroxy, and alkoxy; $X^1$ is hydrogen, hydroxy, alkyl, alkoxy or together with the carbon to which it is attached forms a carbonyl or an oxime; and $R^8$ and $R^{12}$ are independently hydrogen, alkyl, heteroalkyl, arylalkyl, heteroarylalkyl, or an oxygen protecting group are described.

In another embodiment, the compounds of any of the preceding embodiments wherein $R^3$ is methoxy and $R^7$ is methoxy are described.

In another embodiment, the compounds of any of the preceding embodiments wherein $R^6$ is hydrogen are described.

In another embodiment, the compounds of any of the preceding embodiments wherein $R^2$ is hydrogen are described.

In another embodiment, the compounds of any of the preceding embodiments wherein $R^3$ is methoxy, $R^7$ is methoxy, and $R^6$ is hydrogen are described.

In another embodiment, the compounds of any of the preceding embodiments wherein $R^3$ is methoxy, $R^7$ is methoxy, and $R^2$ is hydrogen are described.

In another embodiment, the compounds of any of the preceding embodiments wherein $R^3$ is methoxy, $R^7$ is methoxy, $R^6$ is hydrogen, and $R^2$ is hydrogen are described.

In another embodiment, the compounds of any of the preceding embodiments wherein $R^2$ is hydroxy; $R^4$ is methoxy; $R^5$ is hydroxy; $R^6$ is hydroxy; $X^1$ is hydroxy; and
$R^1$ is

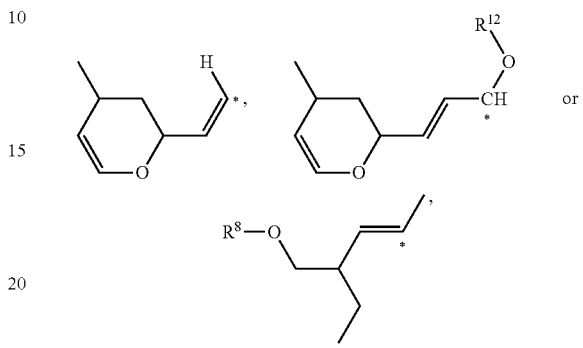

where * shows the point of attachment and $R^8$ and $R^{12}$ are independently hydrogen, alkyl, heteroalkyl, arylalkyl, heteroarylalkyl, or an oxygen protecting group are described.

In another embodiment, the compounds of any of the preceding embodiments wherein $R^2$ is hydroxy; $R^4$ is methoxy; $R^5$ is hydroxy; $R^6$ is hydrogen, hydroxy, alkyl, such as methyl or ethyl, and the like, or alkoxy, such as methoxy or ethoxy, and the like; $X^1$ is hydroxy; and $R^1$ is 4-(R)-hydroxymethyl-hex-2-(Z)-ene-2-yl are described.

In another embodiment, the compounds of any of the preceding embodiments wherein $R^2$ is hydroxy; $R^4$ is methoxy; $R^5$ is hydroxy; $R^6$ is hydroxy; $X^1$ is hydrogen, or epi-hydroxy, or $X^1$ and the attached carbon form a carbonyl; and $R^1$ is 4-(R)-hydroxymethyl-hex-2-(Z)-ene-2-yl are described.

In another embodiment, the compounds of any of the preceding embodiments wherein $R^2$ is hydrogen, hydroxy, or alkyl, such as methyl or ethyl, and the like; $R^4$ is methoxy; $R^5$ is hydroxy; $R^6$ is hydroxy; $X^1$ is hydroxy; and $R^1$ is 4-(R)-hydroxymethyl-hex-2-(Z)-ene-2-yl are described.

In another embodiment, the compounds of any of the preceding embodiments wherein $R^2$ is hydroxy; $R^4$ is hydrogen, hydroxy, alkoxy, such as methoxy or ethoxy, and the like, or alkyl, such as methyl or ethyl, and the like; $R^5$ is hydroxy; $R^6$ is hydroxy; $X^1$ is hydroxy; and $R^1$ is 4-(R)-hydroxymethyl-hex-2-(Z)-ene-2-yl are described.

In another embodiment, the compounds of any of the preceding embodiments wherein $R^2$ is hydroxy; $R^4$ is methoxy; $R^5$ is hydrogen, hydroxy, alkoxy, such as methoxy or ethoxy, and the like, or alkyl, such as methyl or ethyl, and the like; $R^6$ is hydroxy; $X^1$ is hydroxy; and $R^1$ is 4-(R)-hydroxymethyl-hex-2-(Z)-ene-2-yl are described.

In some variations of the embodiments described above, the term alkyl refers to $C_1$-$C_4$ alkyl. In some variations of the embodiments described above, the term alkoxy refers to $C_1$-$C_4$ alkoxy.

In another illustrative embodiment, a method for treating a patient suffering from or in need of relief from cancer, a cancer-related disease or a disease linked to the presence of a population of pathogenic cells is described, the method comprising administering to the patient a therapeutically effective amount of a composition comprising any of the compounds described herein.

In another embodiment, the compounds and methods described herein are used in conjunction with taxol, paclitaxol, and the like, or another compound that binds to taxol site.

The following non-limiting examples are described, each of which may be prepared by the processes described herein:

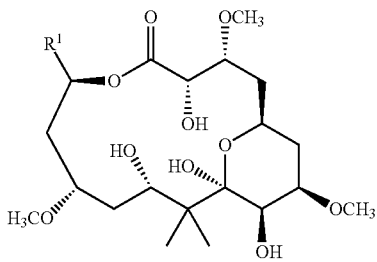

where $R^1$ is

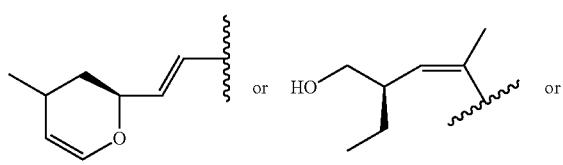

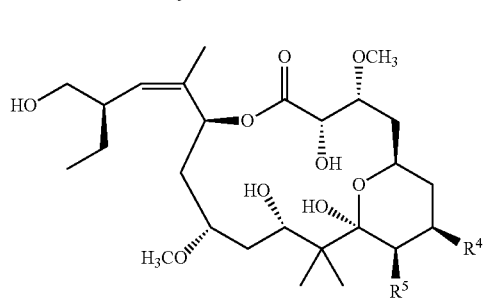

where $R^4$=OH, $CH_3$, H, $OCH_3$ or $CH_2CH_3$; and $R^5$=OH, $CH_3$, H, $OCH_3$ or $CH_2CH_3$;

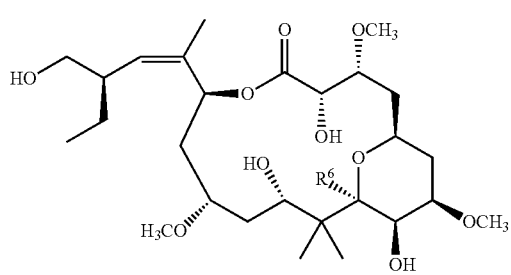

where $R^6$=OH, H, $CH_3$;

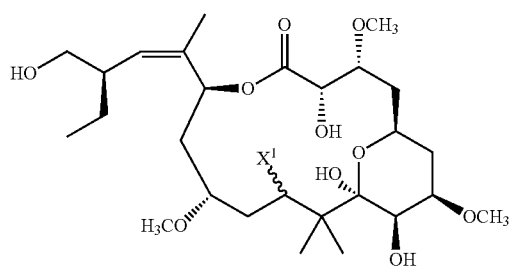

where $X^1$=OH, =O;

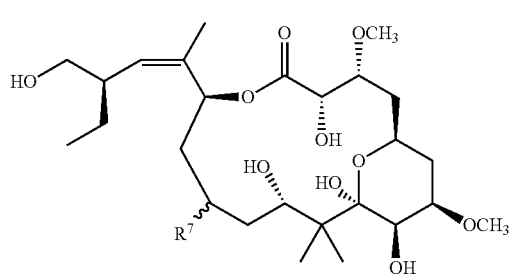

where $R^7$=OH, $OCH_3$, $CH_3$, $CH_2CH_3$, H;

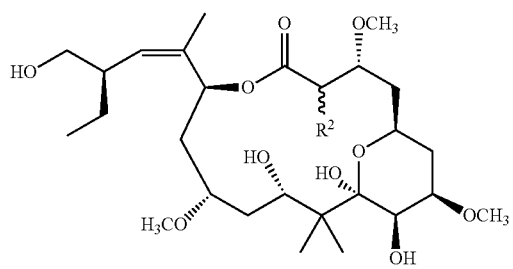

where $R^2$=H, OH, $CH_3$; and

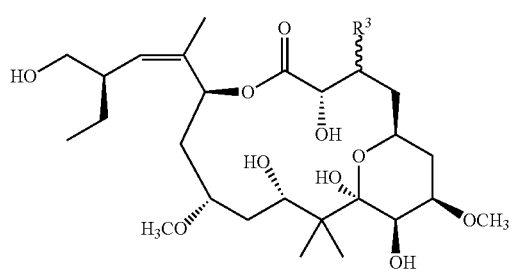

where $R^3$=H, $OCH_3$, $CH_2CH_3$, $CH_3$.

In another embodiment, compounds of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising one or more pharmaceutically acceptable diluents, carriers or excipients and one or more compounds of the invention.

For the treatment of cancer and disease linked to the presence of a population of pathogenic cells, illustratively the compounds described herein may be formulated in a therapeutically effective amount in conventional dosage forms, including one or more carriers, diluents, and/or excipients. Such formulation compositions may be administered by a wide variety of conventional routes in a wide variety of dosage formats, utilizing art-recognized products. See generally, Remington's Pharmaceutical Sciences, (16th ed. 1980). It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein.

In making the formulations of the compounds described herein, a therapeutically effective amount of the compounds herein described, in any of the various forms described herein, may be mixed with an excipient, diluted by an excipient, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is appreciated that the carriers, diluents, and excipients used to prepare the compositions described herein are advantageously GRAS (Generally Regarded as Safe) compounds.

The unitary daily dosage of the compounds described in the invention can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. An effective dose can range from about 1 ng/kg to about 50 mg/kg, from about 0.10 µg/kg to about 10 mg/kg, from about 1 µg/kg to about 5 mg/kg, and from about 10 µg to about 1 mg/kg.

Any effective regimen for administering the composition comprising a compound of the invention can be used. For example, the composition comprising a compound of the invention can be administered as single doses, or it can be divided and administered as a multiple-dose daily regimen. Further, a staggered regimen, for example, one to three days per week can be used as an alternative to daily treatment, and for the purpose of defining this invention such intermittent or staggered daily regimen is considered to be equivalent to every day treatment and within the scope of this invention.

The compounds described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The compounds described herein may be capable of existing as geometric isomers. Accordingly, it is to be understood that the present invention includes pure geometric isomers or mixtures of geometric isomers.

It is appreciated that the compounds described herein may exist in unsolvated forms as well as solvated forms, including hydrated forms. In general, the solvated forms are equivalent to unsolvated forms and are encompassed within the scope of the present invention. The compounds of the present invention may exist in multiple crystalline or amorphous forms. In general, all physical forms are equivalent for the uses contemplated by the present invention and are intended to be within the scope of the present invention.

It is also appreciated that in the foregoing embodiments, certain aspects of the compounds are presented in the alternative, such as selections for any one or more of $X^1$, $R^1$, $R^2$, $R^3$, $R^4$, $R^5$, $R^6$, $R^7$, $R^8$, $R^9$, $R^{10}$, $R^{11}$, $R^{12}$. It is therefore to be understood that various alternate embodiments of the invention include individual members of those lists, as well as the various subsets of those lists. Each of those combinations are to be understood to be described herein by way of the lists.

Additional features of the present invention will become apparent to those skilled in the art upon consideration of the following description of illustrative embodiments for carrying out the invention.

Methods

General Experimental Methods. All moisture sensitive reactions were carried out under nitrogen or argon atmosphere. Anhydrous solvents were obtained as follows: THF, diethyl ether and benzene, distilled from sodium and benzophenone; dichloromethane, pyridine, triethylamine, and diisopropylethylamine, distilled from $CaH_2$. All other solvents were HPLC grade. Column chromatography was performed with 240-400 mesh silica gel under low pressure of 5-10 psi. TLC was carried out with silica gel plates. $^1H$ and $^{13}C$ NMR spectra were recorded on 500 or 400 MHz spectrometers. Infrared spectra were recorded on a FTIR instrument.

Example 1

Olefin (6). To the solution of (−)-2,3-O-isopropylidene-D-threitol (4) (5.5 g, 34 mmol) in THF (60 mL) was added NaH (60%, 1.49 g, 37 mmol) at 0° C., and the reaction was warmed up to 23° C. over 1 h. PMBCl (4.85 mL, 34 mmol) was added at 23° C. and the reaction mixture was stirred for 1.5 h and was quenched with aqueous $NH_4Cl$. The mixture was extracted with ether and the organic layer was washed with water and brine. The resulting mixture was dried over $Na_2SO_4$ and concentrated under reduced pressure. Purification by column chromatography provided product (7.5 g, 78%). To a solution of the mono-PMB protected product (87.3 g, 0.31 mol) in THF (700 mL) was added imidazole (52.6 g, 0.77 mol), Ph$_3$P (122 g, 0.46 mol) and iodine (118 g, 0.46 mol) at 0° C. successively. The resulting mixture was warmed up to 23° C. over 2 h and stirred overnight and then quenched by 10% aqueous Na$_2$S$_2$O$_3$. The mixture was extracted with ether and the organic layer was washed with water and brine. The resulting mixture was dried over Na$_2$SO$_4$ and concentrated under reduced pressure. Purification by column chromatography provided (106 g, 88%) iodide as a colorless oil. $[\alpha]^{23}_D$=+12.2 (c 2.21, CHCl$_3$); IR (thin film, cm$^{-1}$) 2986, 1612, 1514, 1091, 821; $^1$H NMR (500 MHz, CDCl$_3$), δ 7.23 (2H, d, J=6.5 Hz), 6.88 (2H, d, J=6.5 Hz), 4.51 (2H, s), 3.94 (1H, dt, J=2.5, 5.0 Hz), 3.83 (1H, dt, J=3.0, 7.5 Hz), 3.81 (3H, s), 3.63 (1H, dd, 10.0, 5.0 Hz), 3.59 (1H, dd, J=10.0, 5.0 Hz), 3.33 (3H, dd, J=5.0, 10.5 Hz), 3.26 (3H, dd, J=5.5, 10.5 Hz), 1.46 (3H, s), 1.41 (3H, s); $^{13}$C NMR (125 MHz, CDCl$_3$) δ 159.3, 129.9, 129.4, 113.9, 109.8, 80.1, 77.7, 73.3, 70.2, 55.3, 27.4, 27.3, 6.5; MS (EI, m/z) [M]$^+$392.04.

To a solution of the above iodide (34.3 g, 87 mmol) in THF (100 mL) was added HMPA (62 mL) and CuI (3.4 g, 17.2 mmol) at 23° C. The resulting mixture was cooled to −30° C. and vinylmagnesium bromide (173 mL, 1M in THF, 173 mmol) was added dropwise at that temperature over 1 h. The resulting mixture was stirred at −30° C. for 1 h and then warmed up to 10° C. and then quenched with aqueous NH$_4$Cl. The organic layer was separated and the aqueous layer was extracted with Et$_2$O, the combined organic layer was washed with brine, dried over Na$_2$SO$_4$ and concentrated in vacuo. Column chromatography provided product 6 (21.6 g, 85%). $[\alpha]^{23}_D$=+ 15.0 (c 3.05, CH$_2$Cl$_2$); IR (thin film, cm$^{-1}$) 3075, 2985, 2933, 2906, 2864, 2838, 1613, 1514, 1369, 1248, 1172, 1086, 1036, 917; $^1$H NMR (400 MHz, CDCl$_3$) δ 7.25 (2H, d, J=8.5 Hz), 6.88 (2H, d, J=8.7 Hz), 5.82 (1H, m), 5.06-5.13 (2H, m), 4.53 (1H, d, J=11.8 Hz), 4.49 (1H, d, J=11.8 Hz), 3.86 (2H, m), 3.79 (3H, s), 2.36 (2H, m), 1.41 (3H, s), 1.40 (3H, s); $^{13}$C NMR (100 MHz, CDCl$_3$) δ 159.1, 133.7, 130.0, 129.2, 117.5, 113.7, 108.8, 79.5, 77.3, 73.1, 70.0, 55.2, 37.3, 27.1, 26.9; MS (ESI, m/z) [M+Na]$^+$315.0; HRMS (ESI) [M+Na]$^+$ calcd for C$_{17}$H$_{24}$O$_4$Na 315.1572, found 315.1571.

Example 2

Methyl ether (7) To the obtained olefin 6 (31.5 g, 108 mmol) in methanol (500 mL) was added 10% HCl (66 mL) at 0° C. and the mixture was stirred at 23° C. for 12 h. The reaction was then quenched with Na$_2$CO$_3$ (11.4 g, 108 mmol) and concentrated to give the crude diol which was used for the next step without further purification. The crude diol (57 g, 226 mmol) was dissolved in MeCN (1.3 L), and NaHCO$_3$ (109 g, 1.3 mol) and iodine (125 g, 490 mmol) was added successively at 0° C. The resulting mixture was warmed up to 23° C. over 3 h and then quenched by 10% aqueous Na$_2$S$_2$O$_3$ and extracted with ethyl acetate. The combined organic layer was washed with brine and concentrated in vacuo. Column chromatography provided product (70.4 g, 82.4% for 2 steps) as a solid. mp 60-62° C.; $[\alpha]^{23}_D$−24 (c 2.64, CHCl$_3$); $^1$H NMR (500 MHz, CDCl$_3$) δ 7.30 (2H, m), 6.87 (2H, m), 4.53-4.48 (3H, m), 4.26 (0.75H, m), 4.15 (0.75H, dd, J=4.0, 9.0 Hz), 4.09 (0.25H, m), 3.95 (0.25H, dd, J=4.5, 9.0 Hz), 3.75 (2H, m), 3.36 (0.5H, m), 3.33-3.27 (1.5H, m), 3.07 (1H, s), 2.35 (0.25H, ddd, J=14.0, 7.0, 7.0 Hz), 2.20 (0.75H, dd, J=5.5, 14.0 Hz), 1.86 (1H, m); $^{13}$C NMR (125 MHz, CDCl$_3$) δ 159.5, 129.6, 129.5, 114.0, 109.8, 81.0, 78.0, 74.0, 73.6, 73.0, 68.7, 68.6, 55.3, 42.3, 40.8, 11.2, 10.7; IR (thin film, cm$^{-1}$) 3440, 2931, 1612, 1513, 1071, 820; To the solution of the alcohol (24.5 g, 64.8 mmol) in CH$_2$Cl$_2$ (240 mL) was added proton sponge (17.3 g, 81 mmol) and Me$_3$OBF$_4$ (11.7 g, 79 mmol) at 0° C. The reaction mixture was then warmed up to 23° C. and stirred over night. The solid was removed by filtration and the organic layer was washed with aqueous NaHCO$_3$, water and brine, and dried over Na$_2$SO$_4$ and concentrated in vacuo. Column chromatography provided the methyl ether 7 (22 g, 87%). It's a mixture (dr 4:1). $[\alpha]^{23}_D$−41.8 (c 1.83, CH$_2$Cl$_2$); IR (thin film, cm$^{-1}$) 2929, 2902, 2864, 2835, 1612, 1513, 1462, 1247, 1085, 1034, 820; $^1$H NMR (400 MHz, CDCl$_3$) δ 7.27 (2H, d, J=8.1 Hz), 6.87 (2H, d, J=8.6 Hz), 4.56 (1H, d, J=11.7 Hz), 4.45 (0.2H, d, J=11.7 Hz), 4.44 (0.8H, d, J=11.7 Hz), 4.23 (0.8H, m), 4.18 (1H, m), 4.06 (0.2H, m), 3.94 (0.8H, m), 3.89 (0.2H, m), 3.79 (3H, s), 3.71-3.67 (0.2H, m), 3.63 (0.8H, dd, J=5.0, 9.9 Hz), 3.58 (1H, dd, J=6.8, 10.1 Hz), 3.39-3.32 (1.5H, m), 3.30 (2.4H, s), 3.28 (0.6H, s), 3.24-3.21 (1H, m), 2.35 (0.8H, m), 2.19 (0.2H, m), 2.04 (0.2H, ddd, J=2.3, 4.7, 13.7 Hz), 1.69 (0.8H, ddd, J=4.6, 9.1, 13.5 Hz); $^{13}$C NMR (100 MHz, CDCl$_3$) δ 159.1, 130.3, 129.3, 113.6, 82.6, 81.8, 81.7, 80.9, 78.3, 77.2, 76.8, 72.9, 68.7, 68.3, 57.2, 57.1, 55.2, 37.8, 36.2, 11.0, 9.9; MS (ESI, m/z) [M=Na]$^+$415.1; HRMS (ESI) m/z [M+Na]$^+$ calcd for C$_{15}$H$_{21}$O$_4$INa 415.0382, found 415.0392.

Example 3

MOM ether (8) To a solution of the obtained methyl ether 7 (46.2 g, 118 mmol) in 95% ethanol (610 mL) was added zinc dust (59.4 g, 910 mmol). The reaction mixture was stirred at 80° C. for 6 h and cooled down to 23° C. The solid was removed by filtration and rinsed with EtOAc. The filtrate was concentrated in vacuo and purified by column chromatography to provide the product (31 g, 99%) as a colorless oil. $[\alpha]^{23}_D$-8.04 (c 2.55, CHCl$_3$); IR (thin film, cm$^{-1}$) 3457, 2930, 1716, 1612, 1514, 1088, 824; $^1$H NMR (500 MHz, CDCl$_3$) δ 7.25 (2H, d, J=8.4 Hz), 6.88 (2H, d, J=8.4 Hz), 5.82 (1H, m), 5.07 (2H, m), 4.48 (3H, s), 3.76 (3H, m), 3.54-3.46 (2H, m), 3.39 (3H, s), 3.31 (1H, m), 2.38 (1H, m), 2.28 (1H, m); $^{13}$C NMR (125 MHz, CDCl$_3$) δ 159.3, 134.3, 130.1, 129.5, 117.5, 113.7, 80.5, 73.1, 71.4, 70.7, 58.2, 55.3, 34.3; MS (ESI, m/z) [M+Na]$^+$289.1. To a stirred solution of the alcohol (31 g, 116 mmol) in CH$_2$Cl$_2$ (300 mL) was added diisopropylethylamine (69.7 mL 371 mmol) and MOMCl (23.6 mL, 309 mmol) successively and the resulting mixture was stirred over night and quenched with water. The organic layer was separated, washed with brine, dried over Na$_2$SO$_4$ and concentrated in vacuo. Column chromatography provided the MOM ether 8 (32 g, 88%) as a colorless oil. $[\alpha]^{23}_D$ −13.6 (c 2.95, CHCl$_3$); $^1$H NMR (500 MHz, CDCl$_3$) δ 7.25 (2H, d, J=9.0 Hz), 6.87 (2H, d, J=9.0 Hz), 5.83 (1H, m), 5.06 (2H, m), 4.78 (1H, d, J=6.5 Hz), 4.69 (1H, d, J=6.5 Hz), 4.78 (1H, A of AB, J=11.5 Hz), 4.45 (1H, B of AB, J=11.7 Hz), 3.80 (s, 3H), 3.77 (1H, m), 3.63 (1H, dd, J=4.5, 9.5 Hz), 3.56 (1H, dd, J=6.0, 10.0 Hz), 3.42 (1H, m), 3.40 (3H, s), 3.38 (3H, s), 2.35 (1H, m), 2.28 (1H, m); $^{13}$C NMR (125 MHz, CDCl$_3$) δ 159.2, 135.3, 130.3, 129.3, 117.1, 113.8, 97.1, 80.5, 73.0, 65.5, 58.7, 55.7, 53.3, 34.5; MS (ESI, m/z) [M+Na]$^+$333.0.

Example 4

Alcohol (9) To the solution of thus obtained MOM ether 8 (7 g, 22.5 mmol) in acetone/H$_2$O (106 mL/13 mL) was added NMO (5.3 g, 45 mmol) and OsO$_4$ (2.5 w % in t-BuOH, 8.3 mL, 0.69 mmol). The resulting mixture was stirred at 23° C. for 3 h and quenched with saturated aqueous NaHSO$_3$ (42 mL). The solid was removed by filtration and the filtrate was extracted with EtOAc. The combined organic layer was washed with brine, dried over $Na_2SO_4$ and concentrated in vacuo. To a solution of ⅓ of the crude diol (2.6 g, 7.49 mmol) in $THF/H_2O$ (58 mL/14 mL) was added $NaIO_4$ (3.85 g, 18 mmol) at 23° C. and stirred for 2 h. The solid was removed by filtration and the filtrate was extracted with $Et_2O$. The combined organic layer was washed with buffer solution (pH=7), water and brine, and dried over $Na_2SO_4$ and concentrated in vacuo. The aldehyde was used without further purification. To the solution of (+)-$Ipc_2BOMe$ (2.84 g, 9.0 mmol) in $Et_2O$ (32 mL) was added allylmagnesium bromide$_{S-5}$ (1M in $Et_2O$, 8.2 mL) dropwise at 0° C. The resulting mixture was warmed up to 23° C. over 1 h. The solid was removed by filtration. And to the filtrate was added thus obtained crude aldehyde in $Et_2O$ (15 mL) via cannula at −78° C. over 5 min, and the mixture was stirred for 2 h at −78° C. Then the reaction was quenched with aqueous NaOH (2 M, 12 mL) and $H_2O_2$ (30%, 5 mL) and slowly warmed up to 23° C. over night. The resulting mixture was extracted with $Et_2O$ and the combined organic layer was washed with water and brine, dried over $Na_2SO_4$ and concentrated in vacuo. The crude material was passed through a short column to get the crude product. $^1H$ NMR (400 MHz, $CDCl_3$) δ 7.23 (2H, d, J=8.5 Hz), 6.86 (2H, d, J=8.5 Hz), 5.81 (1H, m), 5.09 (2H, m), 4.79 (1H, d, J=6.8 Hz), 4.67 (1H, d, J=6.8 Hz), 4.46 (1H, d, J=11.6 Hz), 4.43 (1H, d, J=11.6 Hz), 3.86 (2H, m), 3.78 (3H, s), 3.62 (2H, m), 3.51 (1H, dd, J=6.6, 10.3 Hz), 3.44 (3H, s), 3.36 (3H, s), 3.28 (1H, br s), 2.21 (2H, m), 1.72 (1H, m), 1.49 (1H, dt, J=14.5, 9, 3 Hz); $^{13}C$ NMR (100 MHz, $CDCl_3$) δ 159.1, 134.7, 130.0, 129.2, 117.4, 113.7, 96.8, 81.3, 77.2, 73.0, 70.3, 69.3, 58.4, 55.6, 55.2, 42.1, 35.8;

Example 5

TBS ether (10) To a solution of the crude diastereomeric mixture (2.05 g, 5.78 mmol) in DMF (15 mL) was added imidazole (720 mg, 10.6 mmol), DMAP (70 mg, 0.6 mmol) and TBSCl (1.06 g, 7.03 mmol) at 23° C. and then the mixture was stirred over night. To the resulting mixture was added water and EtOAc and the organic layer was washed with water and brine, dried over $Na_2SO_4$, concentrated in vacuo. Column chromatography provided the pure diastereomeric isomer 10 (2.6 g, 74% over 4 steps, dr 94:6): $[\alpha]^{23}{}_D$-4.8 (c 2.69, $CH_2Cl_2$); IR (thin film, cm$^{-1}$) 3075, 2953, 2930, 2895, 1856, 1612, 1513, 1249, 1099, 1039, 835; $^1H$ NMR (400 MHz, $CDCl_3$) δ 7.24 (2H, d, J=8.6 Hz), 6.86 (2H, d, J=8.6 Hz), 5.82 (1H, m), 5.06 (1H, d, J=6.5 Hz), 5.03 (1H, s), 4.79 (1H, d, J=6.8 Hz), 4.65 (1H, d, J=6.8 Hz), 4.45 (2H, s), 3.81 (2H, m), 3.80 (3H, s), 3.62 (1H, dd, J=4.9, 9.9 Hz), 3.56 (1H, dd, J=6.2, 9.7 Hz), 3.47 (1H, m), 3.37 (3H, s), 3.36 (3H, s), 2.28 (1H, m), 2.23 (1H, m), 1.75 (1H, m), 1.64 (1H, m), 0.87 (9H, s), 0.05 (3H, s), 0.03 (3H, s); $^{13}C$ NMR (100 MHz, $CDCl_3$) δ 159.0, 134.9, 130.3, 129.2, 116.9, 113.6, 96.7, 77.5, 72.9, 69.8, 68.9, 58.0, 55.7, 55.2, 41.9, 36.7, 25.8, 17.9, −4.4, −4.6; MS (ESI, m/z) [M+Na]$^+$491.18; HRMS (ESI) [M+Na]$^+$ calcd for $C_{25}H_{44}O_6SiNa$ 491.2805, found 491.2806.OPMB Example 6

Unsaturated ester (11) To the solution of thus obtained silyl ether 10 (11 g, 23.5 mmol) in acetone/water (120 mL/15 mL) was added $OsO_4$ (2.5 w % in t-BuOH, 2.87 mL, 0.24 mmol) and NMO (3.31 g, 28.5 mmol) at 23° C. and the reaction mixture was stirred at that temperature for 5 h. The solid was removed and the filtrate was extracted with EtOAc. The combined organic layer was washed with water and brine, dried over $Na_2SO_4$ and concentrated in vacuo. To the solution of the crude diol in $THF/H_2O$ (100$_{S-6}$ mL/25 mL) was added $NaIO_4$ (6.03 g, 28.2 mmol) and the reaction mixture was stirred at 23° C. for 3 h. The solid was removed by filtration and the filtrate was extracted with EtOAc. The combined organic layer was washed with water and brine, dried over $Na_2SO_4$ and concentrated in vacuo. The crude aldehyde was used without further purification. To the solution of $(O\text{-cresol})_2P(O)CH_2CO_2Et$ (9.29 g, 29.4 mmol) in THF (210 mL) was added NaI (3.45 g, 23 mmol) and NaH (60% in mineral oil, 1.03 g, 25.8 mmol) at 0° C. and it was stirred at 0° C. for 10 min and cooled down to −78° C. To the resulting mixture was added the aldehyde in THF (50 mL) dropwise at −78° C. The reaction mixture was stirred at −78° C. for 2 h and warmed up to −50° C. and then quenched with aqueous $NH_4Cl$ and extracted with EtOAc. The combined organic layer was washed with water and brine, dried over $Na_2SO_4$ and concentrated in vacuo. Column chromatography provided the Z isomer 11 (9.9 g, 78%) and E isomer (1.4 g, 11%). Z isomer: $[\alpha]^{23}{}_D$ −9.5 (c 2.1, $CH_2Cl_2$); IR (thin film, cm$^{-1}$) 2953, 2930, 2897, 2857, 1718, 1514, 1250, 1180, 1098, 1039; $^1H$ NMR (400 MHz, $CDCl_3$) δ 7.24 (2H, d, J=8.5 Hz), 6.86 (2H, d, J=8.5 Hz), 6.37 91H, dt, J=11.6, 7.0 Hz), 5.84 (1H, d, J=m 11.6 Hz), 4.78 (1H, d, J=6.8 Hz), 4.64 (1H, d, J=6.8 Hz), 4.45 (2H, s), 4.14 (2H, q, J=7.2 Hz), 3.96 (1H, m), 3.79 (3H, s), 3.61 (1H, dd, J=4.7, 9.8 Hz), 3.55 (1H, dd, J=6.3, 9.8 Hz), 3.46 (1H, m), 3.37 (3H, s), 3.36 (3H, s), 2.97 (1H, m), 2.82 (1H, m), 1.68 (2H, m), 1.27 (3H, t, J=7.3 hz), 0.86 (9H, s), 0.05 (3H, s), 0.04 (3H, s); $^{13}C$NMR (100 MHz, $CDCl_3$) δ 166.2, 159.0, 146.2, 130.3, 129.1, 121.0, 113.6, 96.6, 77.4, 76.5, 72.9, 69.7, 68.4, 59.7, 58.2, 55.7, 55.2, 37.2, 36.1, 25.7, 17.9, 14.2, −4.5, −4.7; MS (ESI, m/z) [M+Na]$^+$563.19; HRMS (ESI) [M+Na]$^+$ calcd for $C_{28}H_{48}O_8SiNa$ 563.3016, found 563.3021.

Example 7

Acetonide (12) To the solution of the Z unsaturated olefin 11 (9.89 g, 18.3 mmol) in t-$BuOH/H_2O$ (92 mL/92 mL) was added AD-mix-α (25.7 g) and $CH_3SO_2NH_2$ (1.74 g) at 0° C. The reaction mixture was stirred at that 0° C. for 4 days and then quenched with $NaHSO_3$ and extracted with EtOAc. The combined organic layer was washed with water and brine, dried over $Na_2SO_4$ and concentrated in vacuo. The crude material was passed through a short silica gel column to provide the crude diastereomeric mixture (10.2 g, 97%), which could be separated in next step. To the solution of crude diol in $CH_2Cl_2$ (100 mL) was added PPTS (335 mg, 1.33 mmol) and 2-methoxypropene (4.4 mL, 46 mmol) at 23° C. and the reaction mixture was stirred for 30 min. The reaction solvent was removed in vacuo and purification by column chromatography provided the major product 12 (8.71 g) and minor product (1.17 g, overall 95%). The major isomer: $[\alpha]^{23}{}_D$+20.0 (c 1.89, $CH_2Cl_2$); IR (thin film, cm$^{-1}$) 2982, 2953, 2932, 2896, 2856, 1757, 1513, 1463, 1249, 1099, 1039, 837; $^1H$ NMR (400 MHz, $CDCl_3$) δ 7.23 (2H, d, J=8.5 Hz), 6.86 (2H, d, J=8.6 Hz), 4.76 (1H, d, J=6.8 Hz), 4.64 (1H, d, J=6.8 Hz), 4.53 (1H, s), 4.50 (1H, m), 4.44 (2H, s), 4.24-4.14 (2H, m), 4.06 (1H, m), 3.79 (3H, s), 3.76 (1H, m), 3.60 (1H, dd, J=4.5, 10.0 Hz), 3.50 (1H, dd, J=6.5, 9.9 Hz), 3.43 (1H, m), 3.36 (3H, s), 3.35 (3H, s), 1.71-1.64 (3H, m), 1.58 (3H, s), 1.51 (1H, m), 1.35 (3H, s), 1.25 (3H, t, J=7.2 hz), 0.88 (9H, s), 0.07 (3H, s), 0.05 (3H, s); $^{13}C$ NMR (100 MHz, $CDCl_3$) δ 170.4, 159.0, 130.2, 129.1, 113.6, 110.4, 96.5, 77.2, 76.9, 74.1, 72.9, 69.5, 66.4, 60.8, 58.5, 55.6, 55.2, 39.0, 37.6, 27.0, 25.8, 25.7, 17.9, 14.1, −4.3, −4.9; MS (ESI, m/z) [M+Na]$^+$ 637.21; HRMS (ESI) [M+Na]$^+$ calcd for $C_{31}H_{54}O_{10}SiNa$ 637.3384, found 637.3392.

Example 8

Enone (2) To the solution of thus obtained ester 12 (1.47 g, 2.39 mmol) in $CH_2Cl_2$ (30 mL) was added DIBAL-H (1M in $CH_2Cl_2$, 2.5 mL, 2.5 mmol) dropwise at −78° C. The resulting mixture was stirred at that temperature for 1 h and quenched with $NH_4Cl$. The solid was removed by filtration and the filtrate was extracted with EtOAc. The combined organic layer was washed with brine, dried over $Na_2SO_4$, and concentrated in vacuo. The crude material was passed through a short silica gel pad to provide the crude aldehyde, which was then dissolved in THF (50 mL). To the solution was added isopropenylmagnesium bromide (0.5 M in THF, 26.9 mL, 13.4 mmol) dropwise at 0° C. and kept at 0° C. for 15 min before quenched with aqueous $NH_4Cl$. The resulting mixture was extracted with EtOAc and the combined organic layer was washed with water and brine, dried over $Na_2SO_4$ and concentrated in vacuo. Column chromatography provided the diastereomeric mixture (1.21 g, 86%). To the solution of the obtained alcohol mixture (7.02 g, 11.4 mmol) in $CH_2Cl_2$ (40 mL) was added Dess-Martin periodinane (5.83 g, 13.7 mmol) and $NaHCO_3$ (3.46 g, 41.2 mmol) at 23° C. The reaction mixture was stirred for 30 min and quenched with saturated aqueous $Na_2S_2O_3$ (20 mL) and saturated aqueous $NaHCO_3$ (30 mL). The aqueous layer was extracted with $Et_2O$ and the combined organic layer was washed with water and brine, dried over $Na_2SO_4$ and concentrated in vacuo. Column chromatography provided the enone 2 (6.28 g, 90%). $[\alpha]^{23}_D$ +29.3 (c 2.4, $CH_2Cl_2$); IR (thin film, $cm^{-1}$) 2953, 2931, 2894, 2856, 1693, 1513, 1378, 1249, 1100, 1073, 835; $^1$HNMR (400 MHz, $CDCl_3$) δ 7.22 (2H, d, J=8.5 Hz), 6.85 (2H, d, J=8.6 Hz), 5.88 (1H, s), 5.84 (1H, d, J=1.1 Hz), 5.29 (1H, d, J=7.1 Hz), 4.74 (1H, d, J=6.8 Hz), 4.62 (1H, d, J=6.8 Hz), 4.58 (1H, m), 4.43 (2H, s), 4.01 (1H, m), 3.78 (3H, s), 3.73 (1H, dt, J=6.7, 4.1 Hz), 3.58 (1H, dd, J=4.2, 9.9 Hz), 3.48 (1H, dd, J=6.6, 9.9 Hz), 3.37 (1H, m), 3.34 (3H, s), 3.32 (3H, s), 1.87 (3H, s), 1.60 (1H, m), 1.58 (3H, s), 1.40 (1H, m), 1.37 (3H, s), 0.87 (9H, s), −0.07 (3H, s), −0.04 (3H, s); $^{13}$C NMR (100 MHz, $CDCl_3$) δ 197.0, 159.0, 144.0, 130.2, 129.1, 125.3, 113.6, 109.6, 96.6, 78.6, 77.2, 76.9, 74.5, 72.9, 69.5, 66.3, 58.5, 55.6, 55.1, 39.0, 38.1, 27.3, 25.8, 25.5, 17.9, 17.8, −4.3, −4.9; MS (ESI, m/z) $[M+Na]^+$633.16; HRMS (ESI) $[M+Na]^+$ calcd for $C_{32}H_{54}O_9SiNa$ 633.3435, found 633.3433.

Example 9

TES ether (14) To the solution of the alcohol 5 (390 mg, 1.41 mmol) in $CH_2Cl_2$ (15 mL) was added 2,6-lutidine (0.63 mL, 5.36 mmol) and TESOTf (0.80 mL, 3.55 mmol). The resulting mixture was stirred for 5 min and water and EtOAc was added. The organic layer was washed with water and brine, dried over $Na_2SO_4$ and concentrated in vacuo. The crude material was passed through a silica gel pad to provide the crude silyl ether (495 mg, 90%). $^1$H NMR (400 MHz, $CDCl_3$) δ 7.34 (4H, m), 7.28 (1H, m), 5.81 (1H, m), 5.13-5.07 (2H, m), 4.92 (1H, d, J=10.2 Hz), 4.54 (1H, dd, J=5.0, 8.1 Hz), 4.51 (2H, s), 3.32 (3H, m), 2.57 (1H, m), 2.37 (1H, m), 2.16 (1H, m), 1.71 (3H, d, J=1.0 Hz), 1.66 (1H, m), 1.23 (2H, m), 0.94 (9H, t, J=7.8 Hz), 0.85 (3H, t, J=7.5 Hz), 0.56 (6H, q, J=7.8 Hz); $^{13}$C NMR (100 MHz, $CDCl_3$) δ 139.2, 138.6, 135.8, 128.2, 127.5, 127.4, 126.7, 116.3, 73.5, 73.0, 70.6, 41.5, 39.1, 25.3, 17.9, 11.6, 6.8, 4.7.

Example 10

Alcohol (15) The TES ether was dissolved in t-BuOH/Acetone/$H_2O$ (4 mL/4 mL/1 mL). To the solution was added NMO (0.41 g, 3.53 mmol) and $OsO_4$ (2.5 w % in t-BuOH, 0.88 mL, 0.074 mmol) at 0° C. and it was stirred at this temperature for 2 h before being quenched with aqueous $NaHSO_3$. The resulting mixture was extracted with EtOAc and the organic layer was washed with brine, concentrated in vacuo and dissolved in $CH_2Cl_2$ (10 mL). To the solution was added pyridine (0.3 mL, 3.7 mmol) and $Pb(OAc)_4$ (0.66 g, 1.49 mmol) at 23° C. and stirred for 30 min. The solid was removed by filtration and the filtrate was extracted with EtOAc. The organic layer was washed with water and brine, dried over $Na_2SO_4$ and concentrated in vacuo. The crude material was passed through a silica gel pad to give crude aldehyde (374 mg, 74%, 2 steps). To the solution of (−)-$Ipc_2BOMe$ (788 mg, 2.49 mmol) in $Et_2O$ (12 mL) was added allylmagnesium bromide (1 M in $Et_2O$, 2.22 mL, 2.22 mmol) dropwise at 0° C. The resulting mixture was warmed up to 23° C. over 2 h. The solid was removed by filtration and the filtrate was cooled down to −78° C. To the filtrate was added thus obtained crude aldehyde in $Et_2O$ (5 mL) via cannula at −78° C. over 5 min, and the mixture was stirred for 2 h at −78° C. and then quenched with buffer (pH=7) and $H_2O_2$ (30%, 5 mL). The resulting mixture was slowly warmed up to 23° C. over night and extracted with $Et_2O$. The combined organic layer was washed with water and brine, dried over $Na_2SO_4$ and concentrated in vacuo. Column chromatography provided major isomer (374 mg, 83%, dr 5:1).

Example 11

Methyl ether (16) To the solution of the thus made homoallylic alcohol (165 mg, 0.38 mmol) in $CH_2Cl_2$ (3 mL) was added proton sponge (333 mg, 1.56 mmol) and $Me_3OBF_4$ (173 mg, 1.17 mmol) at 23° C. The reaction mixture was stirred for 3 h and the solid was removed by filtration. The filter cake was washed with hexane and the filtrate was washed with $NaHCO_3$, water and brine. The organic phase was dried over $Na_2SO_4$ and concentrated in vacuo. Column chromatography provided methyl ether 13 (153 mg, 93%): $[\alpha]^{23}_D$ −35.3 (c 1.21, $CH_2Cl_2$); IR (thin film, $cm^{-1}$) 3075, 3066, 3029, 2955, 2936, 2876, 2825, 1454, 1239, 1089, 1005, 741; $^1$H NMR (400 MHz, $CDCl_3$) δ7.34 (4H, m), 7.27 (1H, m), 5.86 (1H, m), 5.13-5.07 (2H, m), 4.94 (1H, d, J=10.1 Hz), 4.60 (1H, dd, J=4.6, 8.8 Hz), 4.50 (2H, s), 3.33 (3H, m), 3.32 (3H, s), 2.56 (1H, m), 2.38 (1H, m), 2.23 (1H, m), 1.94 (1H, ddd, J=4.9 8.9 13.8 Hz), 1.69 (3H, d, J=1.0 Hz), 1.62 (1H, m), 1.44 (1H, ddd, J=4.5 7.5, 12.2 Hz), 1.24 (1H, m), 0.92 (9H, t, J=8.0 Hz), 0.84 (3H, t, J=7.4 Hz), 0.56 (6H, q, J=7.9 Hz); $^{13}$C NMR (100 MHz, $CDCl_3$) δ 138.9, 138.6, 134.7, 128.2, 127.5, 127.4, 127.2, 116.9, 77.4, 73.3, 73.0, 67.5, 55.9, 40.1, 39.0, 37.4, 25.3, 17.8, 11.4, 6.9, 4.8; MS (ESI, m/z) $[M+Na]^+$ 469.21; HRMS (ESI) $[M+Na]^+$ calcd for $C_{27}H_{46}O_3SiNa$ 469.3114, found 469.3123.

Example 12

Aldehyde (3) To the solution of the methyl ether 16 (133 mg, 0.30 mmol) in t-BuOH/Acetone/$H_2O$ (1.0 mL/1.0 mL/0.25 mL) was added NMO (0.07 g, 0.60 mmol) and $OsO_4$ (2.5 w % in t-BuOH, 0.15 mL, 0.013 mmol) at 0° C. and it was stirred at this temperature for 2 h before quenched with aqueous $NaHSO_3$. The resulting mixture was extracted with EtOAc and the organic layer was washed with brine, concentrated in vacuo and dissolved in $CH_2Cl_2$ (3 mL). To the solution was added pyridine (0.068 mL, 0.75 mmol) and $Pb(OAc)_4$ (145 mg, 0.052 mmol) at 23° C. and stirred for 30 min. The solid was removed by filtration and the filtrate was extracted with EtOAc. The organic layer was washed with water and brine, dried over Na$_2$SO$_4$ and concentrated in vacuo. The crude material was purified by column chromatography to give the aldehyde 3 (100 mg, 75%, 2 steps): [α]$^{23}_D$-40.1 (c 1.16, CH$_2$Cl$_2$); IR (thin film, cm$^{-1}$) 3029, 2956, 2935, 2876, 1727, 1455, 1085, 1005, 742; $^1$H NMR (400 MHz, CDCl$_3$) δ 9.80 (1H, t, J=1.9 Hz), 7.36-7.25 (5H, m), 4.94 (1H, d, J=10.3 Hz), 4.58 (1H, dd, J=3.6, 9.1 Hz), 4.49 (2H, s), 3.82 (1H, m), 3.34 (3H, s), 3.32 (2H, m), 2.64 (1H, ddd, J=1.6, 4.1, 16.3 Hz), 2.57 (1H, ddd, J=2.7, 7.6, 16.5 Hz), 2.51 (1H, m), 2.08 (1H, m), 1.71 (3H, s), 1.64 (1H, m), 1.45 (1H, ddd, J=3.6, 8.2, 13.7 Hz), 1.21 (1H, dt, J=13.6, 7.7 Hz), 0.92 (9H, t, J=8.0 Hz), 0.82 (3H, t, J=7.7 Hz), 0.56 (6H, q, J=7.7 Hz); $^{13}$C NMR (100 MHz, CDCl$_3$) δ 201.4, 138.6, 138.5, 128.2, 127.5, 127.4, 73.7 73.3, 73.0, 67.1, 56.2, 47.7, 40.1, 39.3, 25.3, 17.9, 11.6, 6.8, 4.7.

Example 13

Aldol product (17) To the solution of the enone 2 (645 mg, 1.06 mmol) in Et$_2$O (200 mL) was added L-Selectride (lithium tri-sec-butylborohydride, 1.0 M in THF, 1.1 mL, 1.1 mmol) at -78° C. and the reaction was kept at that temperature for 10-15 min. To the solution was added thus obtained aldehyde 3 (520 mg, 1.2 mmol) in Et$_2$O (20 mL) at -78° C. The reaction mixture was stirred at -78° C. for 1 h and quenched with NH$_4$Cl. The organic layer was separated and the aqueous layer was extracted with EtOAc. The combined organic layer was washed with water and brine, dried over Na$_2$SO$_4$ and concentrated in vacuo. Column chromatography provided the major isomer 17 and minor isomer (823 mg and 206 mg respectively, 92%, dr 4:1). Major isomer: [α]$^{23}_D$-13.9 (c 1.15, CH$_2$Cl$_2$); IR (thin film, cm$^{-1}$) 2956, 2936, 2879, 2859, 1714, 1514, 1463, 1379, 1249, 1098, 1078, 1038, 836; $^1$H NMR (400 MHz, CDCl$_3$) δ 7.30-7.25 (5H, m), 7.22 (2H, d, J=8.5 Hz), 6.84 (2H, d, J=8.5 Hz), 5.12 (1H, d, J=6.7 Hz), 4.92 (1H, d, J=10.1 Hz), 4.75 (1H, d, J=6.7 Hz), 4.63 (1H, d, J=6.8 Hz), 4.54 (2H, m), 4.46 (2H, s), 4.43 (2H, s), 4.01 (2H, m), 3.75 (3H, s), 3.59 (2H, dd, J=4.3, 10.0 Hz), 3.48 (1H, dd, J=6.7, 9.9 Hz), 3.39 (1H, m), 3.35 (6H, s), 3.30 (2H, m), 3.29 (3H, s), 2.51 (1H, m), 2.05 (1H, m), 1.69 (3H, s), 1.64-1.61 (4H, m), 1.57-1.42 (2H, m), 1.50 (3H, s), 1.33 (3H, s), 1.23 (2H, m), 1.18 (3H, s), 1.10 (3H, s), 0.94 (1H, m), 0.89 (9H, t, J=8.0 Hz), 0.87 (12H, s), 0.83 (3H, t, J=7.5 Hz), 0.54 (6H, q, J=8.0 Hz), 0.08 (3H, s), 0.05 (3H, s); $^{13}$C NMR (100 MHz, CDCl$_3$) δ 210.2, 159.0, 138.9, 138.5, 130.2, 129.1, 128.2, 127.4, 127.3, 127.2, 113.6, 109.1, 96.6, 79.2, 77.3, 76.9, 76.5, 74.3, 73.2, 73.0, 72.9, 72.8, 69.5, 67.3, 66.4, 58.5, 56.2, 55.6, 55.0, 51.3, 39.14, 39.05, 33.3, 27.6, 25.8, 25.3, 20.8, 18.8, 17.94, 17.87, 11.6, 6.8, 4.7, -4.3, -4.9; MS (ESI, m/z) [M+Na]$^+$1083.32; HRMS (ESI) [M+Na]$^+$ calcd for C$_{58}$H$_{100}$O$_{13}$Si$_2$Na 1083.6600, found 1083.6611.

Example 14

Alcohol (18) To the solution of the major aldol product 17 (30 mg, 0.028 mmol) in THF/H$_2$O (9:1, 1.8 mL) was added DDQ (2 mg, 0.01 mmol). The reaction mixture was stirred for 3 h at 23° C. and CH$_2$Cl$_2$ (7 mL), buffer (pH=7, 1.2 mL) and DDQ (30 mg, 0.13 mmol) was added. The resulting mixture was stirred for 8 h at 23° C. and aqueous NaHCO$_3$ was added. The organic layer was separated and the aqueous layer was extracted with EtOAc. The combined organic phase was washed with dilute aqueous NaHCO$_3$, water and brine, dried over Na$_2$SO$_4$ and concentrated in vacuo. Column$_{S-11}$ chromatography gave the alcohol 18 (16 mg, 70%):: [α]$^{23}_D$+17.9 (c 1.3, CHCl$_3$); IR (thin film, cm$^{-1}$) 3443, 2956, 2928, 2855, 1713, 1462, 1378, 1252, 1097, 1074, 836; $^1$HNMR (400 MHz, CDCl$_3$) δ 7.34-7.24 (5H, m), 5.10 (1H, d, J=6.6 Hz), 4.95 (1H, d, J=9.5 Hz), 4.71 (1H, d, J=6.9 Hz), 4.65 (1H, d, J=6.9 Hz), 4.59 (1H, dd, J=4.8, 8.5 Hz), 4.52 (1H, m), 4.47 (2H, m), 4.02-3.95 (2H, m), 3.69 (1H, m), 3.63-3.53 (3H, m), 3.42-3.36 (2H, m), 3.40 (3H, s), 3.35 (3H, s), 3.32 (3H, s), 3.12 (1H, t, J=9.1 Hz), 2.65 (1H, m), 2.02 (1H, m), 1.72 (3H, s), 1.69-1.55 (6H, m), 1.50 (3H, s), 1.20 (2H, m), 1.18 (3H, s), 1.13 (1H, m), 1.09 (3H, s), 0.87 (9H, s), 0.82 (3H, t, J=7.4 Hz), 0.07 (3H, s), 0.05 (3H, s); $^{13}$C NMR (100 MHz, CDCl$_3$) δ 210.6, 139.3, 137.6, 130.9, 128.4, 127.7, 109.2, 97.3, 81.1, 79.1, 78.1, 77.9, 74.3, 73.7, 73.4, 73.2, 66.3, 65.7, 62.4, 58.2, 56.9, 55.7, 51.4, 39.3, 38.9, 38.6, 36.5, 33.5, 29.6, 27.6, 25.8, 24.7, 20.8, 18.9, 18.1, 17.9, 11.8, -4.3, -4.9; MS (ESI, m/z) [M+Na]$^+$849.2; HRMS (ESI) [M+Na]$^+$ calcd for C$_{44}$H$_{78}$O$_{12}$SiNa 849.5160, found 849.5154.

Example 15

Macrolactone (19) To the solution of the alcohol 18 (17.3 mg, 0.021 mmol) in CH$_2$Cl$_2$ (1.9 mL) was added 4 Å molecular sieve, NMO (2.2 mg, 0.021 mmol) and TPAP (1.2 mg, 0.004 mmol) at 0° C. The resulting mixture was stirred at 0° C. for 1 h. The solid was removed by filtration and EtOAc was added to the filtrate. The organic phase was washed with aqueous Na$_2$S$_2$O$_3$, water and brine, concentrated in vacuo and dissolved in t-BuOH (3.3 mL). To the solution was added 2-methyl-2-butene (0.4 mL) and a solution of NaClO$_2$ (32 mg, 0.35 mmol) and NaH$_2$PO$_4$ (35 mg, 0.29 mmol) in H$_2$O (3.3 mL). The resulting mixture was stirred at 23° C. for 25 min. The organic layer was separated and the aqueous layer was extracted with EtOAc. The combined organic phase was washed with water and brine, dried over Na$_2$SO$_4$ and concentrated in vacuo. The crude product was passed through a short silica gel column to obtain the crude seco-acid 9 mg. To the solution of thus obtained seco-acid in toluene (2.4 mL) was added DIPEA (0.05 mL, 0.29 mmol) and 2,4,6-trichlorobenzoyl chloride (18.8 [L, 0.12 mmol) at 23° C. The reaction was stirred for 15 h at that temperature and was added dropwise to a solution of DMAP (22.4 mg, 0.18 mmol) in toluene (25 mL) at 23° C. over 10 h. The resulting mixture was stirred at 23° C. for 36 h and water was added. The organic layer was separated and the aqueous was extracted with EtOAc. The combined organic phase was wash with 0.18% HCl, water and brine, dried over Na$_2$SO$_4$ and concentrated in vacuo. Column chromatography provided product 19 (5.7 mg, 64%): [α]$^{23}_D$-45.7 (c 0.88, CHCl$_3$); IR (thin film, cm$^{-1}$) 2956, 2929, 2856, 1730, 1463, 1379, 1256, 1095, 1076, 1027, 971, 837; $^1$H NMR (400 MHz, CDCl$_3$) δ 7.35-7.22 (5H, m), 5.78 (1H, d, J=8.0 Hz), 5.06 (1H, d, J=10.2 Hz), 4.90 (1H, d, J=6.9 Hz), 4.70 (1H, $_{S-12}$d, J=6.7 Hz), 4.68 (1H, d, J=6.7 Hz), 4.63 (1H, m), 4.53 (1H, d, J=12.1 Hz), 4.47 (1H, d, J=12.1 Hz), 4.08 (1H, m), 3.98 (1H, d, J=5.1 Hz), 3.81 (1H, m), 3.59 (1H, dd, J=4.1, 9.3 Hz), 3.49 (1H, m), 3.40 (3H, s), 3.37 (3H, s), 3.34 (6H, s), 3.20 (1H, m), 2.75 (1H, m), 2.05 (1H, ddd, J=15.2, 5.5, 1.1 Hz), 1.97 (1H, ddd, J=15.2, 9.1, 1.3 Hz), 1.88 (1H, ddd, J=14.5, 6.3, 4.3 Hz), 1.72 (2H, m), 1.66 (3H, s), 1.63 (1H, m), 1.59 (3H, s), 1.53 (1H, m), 1.42 (3H, s), 1.37 (3H, s), 1.32 (1H, m), 1.22 (1H, m), 1.18 (3H, s), 0.88 (9H, s), 0.84 (3H, t, J=7.5 Hz), 0.09 (3H, s), 0.08 (3H, s); $^{13}$C NMR (100 MHz, CDCl$_3$) δ 216.1, 168.8, 138.9, 134.0, 129.8, 128.1, 127.5, 127.2, 110.2, 96.4, 79.4, 77.4, 76.7, 75.4, 74.0, 72.7, 70.6, 66.0, 58.4, 57.4, 56.2, 50.4, 39.5, 39.3, 38.5, 37.9, 35.7, 29.6, 26.7, 25.8, 25.5, 25.2, 24.9, 21.0, 17.9, 11.6, -4.2, -5.0; MS (ESI, m/z) [M+Na]$^+$845.24; HRMS (ESI) [M+Na]$^+$ calcd for C$_{44}$H$_{74}$O$_{12}$SiNa 845.4847, found 845.4840.

Example 16

Methyl ether (20). The macrolactone 19 (13 mg, 0.016 mmol) was dissolved in a mixture of THF (3.6 mL) and 1N HCl (3.6 mL). The resulting mixture was stirred at 23° C. for 9 h. The aqueous layer was extracted with EtOAc and the combined organic phase was washed with aqueous NaHCO$_3$, water and brine, dried over Na$_2$SO$_4$ and concentrated in vacuo. The crude material was passed through a silica gel pad to give the crude product which was then dissolved in CH$_2$Cl$_2$. To the solution was added 2,6-di-tert-butylpyridine (60 μL), Me$_3$OBF$_4$ (24 mg) at 0° C. The reaction was stirred for 4 h and quenched with aqueous NaHCO$_3$. The organic phase was separated and the aqueous layer was extracted with EtOAc. Combined organic phase was washed with water and brine, dried over Na$_2$SO$_4$ and concentrated in vacuo. A simple silica gel column gave 8 mg crude product, which may contains both the macrolactone form and the semi-ketal form. MS (ESI, m/z) [M+Na]$^+$705.29.

Example 17

Peloruside A. To the solution of the methyl ether (4 mg) in methanol (2 mL) was added formic acid (0.1 mL) and a catalytic amount of 10% Pd/C at 23° C. and the resulting mixture was stirred for 1 h. Celite® was added and the solid was removed by filtration. The filtrate S-13 was concentrated in vacuo and was dissolved in THF/4N HCl (1.5 mL/1.5 mL) and was stirred for 3.5 h at 23° C. The reaction mixture was extracted with EtOAc and the combined organic layer was washed with NaHCO$_3$, water and brine, dried over Na$_2$SO$_4$ and concentrated in vacuo. Column chromatography provided the (+)-Peloruside A (1) (1.6 mg, 50%, 2 steps) [α]$^{23}_D$+ 15.1 (c 0.1, CH$_2$Cl$_2$); IR (thin film, cm$^{-1}$) 2957, 2923, 2852, 1742, 1463, 1378, 1151, 1086, 1037, 722; $^1$H NMR (500 MHz, CDCl$_3$) δ 36.79 (1H, br s), 5.69 (1H, d, J=10.6 Hz), 5.05 (1H, d, J=10.5 Hz), 4.91 (1H, m), 4.54 (1H, br d, J=8.2 Hz), 4.47 (1H, s), 4.28 (1H, ddd, J=11.3, 4.4, 2.5 Hz), 4.23 (1H, dd, J=10.6, 5.4 Hz), 4.02 (1H, d, J=2.8 Hz), 3.99 (1H, m), 3.82 (1H, ddd, J=11.5, 5.0, 3.0 Hz), 3.65 (1H, br d, J=10.5), 3.48 (3H, s), 3.39 (3H, s), 3.36 (1H, m), 3.31 (3H, s), 3.01 (1H, br s), 2.70 (1H, d, J=9.3 Hz), 2.62 (1H, m), 2.27 (1H, br s), 2.14 (1H, m), 2.05 (1H, m), 1.79 (1H, ddd, J=12.5, 4.9, 2.5 Hz), 1.78 (1H, m), 1.68 (3H, d, J=1.1 Hz), 1.53 (1H, q, J=12.0 Hz), 1.46-1.40 (2H, m), 1.17 (1H, m), 1.13 (3H, s), 1.10 (3H, s), 0.87 (3H, t, J=7.5 Hz); $^{13}$C NMR (125 MHz, CDCl$_3$) δ 174.0, 136.1, 131.2, 102.0, 78.3, 78.0, 76.0, 73.9, 70.9, 70.3, 67.0, 66.9, 63.5, 59.1, 56.1, 55.7, 43.6, 43.4, 35.8, 33.9, 32.6, 31.7, 24.7, 20.9, 17.5, 15.8, 12.3; MS (ESI, m/z) [M+Na]+ 571.17; HRMS (ESI) [M+Na]$^+$ calcd for C$_{27}$H$_{48}$O$_{11}$Na 571.3094, found 571.3102. IC$_{50}$ (P388 murine leukemia cells) 10 nM.

Example 18 epi-C-11 Peloruside A. epi-C-11 peloruside was prepared in an analogous manner. $^1$H NMR (500 MHz), δ 7.33 (br s, 1H), 5.60 (d, J=10.2 Hz, 1H), 5.09 (d, J=10.4 Hz), 4.92 (br s, 1H), 4.31 (s, 1H), 4.29 (m, 1H), 4.14 (m, 1H), 3.95 (d, J=2.7 Hz, 1H), 3.76 (ddd, J=2.9, 4.8, 9.4 Hz, 1H), 3.67 (m, 2H), 3.54 (d, J=10.7 Hz, 1H), 3.47 (s, 3H), 3.41 (s, 3H), 3.37 (s, 3H), 3.39-3.37 (m, 1H), 2.57 (m, 1H), 2.32 (dt, J=15.5, 11.1 Hz), 2.08 (m, 2H), 2.01-1.96 (m, 2H), 1.80 (m, 2H), 1.76 (m, 3H), 1.57 (t, J=11.8 Hz, 2H), 1.43 (m, 1H), 1.40 (s, 3H), 1.33-1.25 (m, 1H), 1.19 (s, 3H), 0.90 (t, J=7.3 Hz, 3H); $^{13}$C NMR (125 MHz), δ 173.4, 136.1, 131.0, 102.5, 87.8, 83.1, 77.3, 75.1, 72.2, 70.7, 68.8, 67.0, 64.6, 57.1, 56.6, 55.7, 43.5, 43.3, 39.3, 34.4, 33.3, 31.4, 29.7, 24.5, 23.5, 22.3, 17.5, 12.3; IR (cm$^{-1}$) 3412, 2956, 2925, 2876, 2854, 1742, 1424, 1223, 1083, 1000. epi-C-11 was equipotent to peloruside A (10 nM) in the cell proliferation assay.

Example 19

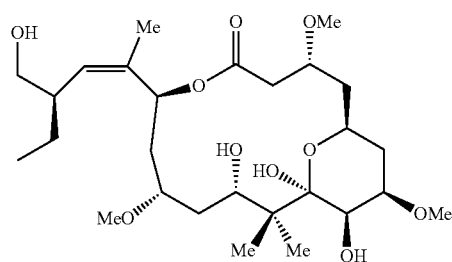

2-des-Hydroxy-Peloruside A. The 2-des-hydroxy compound was prepared using procedures similar to those described herein. It gave an IC$_{50}$ of 120 nM in the cell proliferation assay.

Example 20

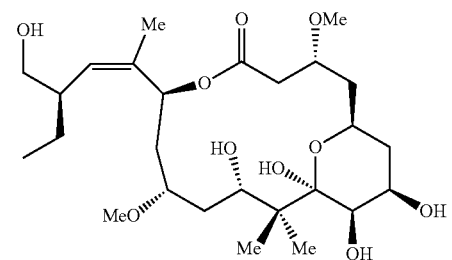

2-des-Hydroxy-7-des-methoxy-7-hydroxy-Peloruside A. The 2-des-hydroxy-7-hydroxy compound was prepared using procedures similar to those described herein. It gave an IC$_{50}$ of 320 nM in the cell proliferation assay.

Example 21

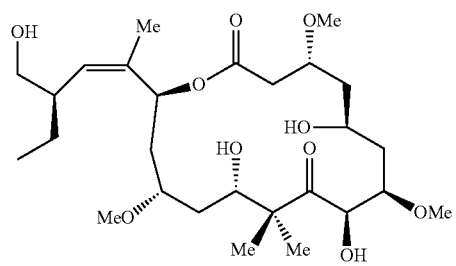

Open Chain Isomer Of 2-Des-Hydroxy-Peloruside A. The des-lactol isomer of 2-des-hydroxy-peloruside A was prepared using procedures similar to those described herein. It gave an IC$_{50}$ of >5 μM in the cell proliferation assay.

What is claimed is:
1. A process for forming a quaternary carbon between a hydroxymethylene or alkoxymethylene carbon and a ketone

(or hemiketal or ketal thereof) carbon or a hydroxymethylene reduction product of said ketone, the process comprising the steps of reacting a first compound containing an α-alkyl-α,β-unsaturated ketone moiety with a source of nucleophilic hydride, wherein the source of nucleophilic hydride is lithium (sec-butyl)$_3$borohydride; and adding a second compound containing an aldehyde to form the quaternary carbon.

2. A process of forming a compound wherein the compound contains a quaternary carbon between a hydroxymethylene or alkoxymethylene carbon and a ketone (or hemiketal or ketal thereof) carbon or a hydroxymethylene reduction product of said ketone comprising the steps of reacting a first compound containing an α-alkyl-α,β-unsaturated ketone moiety with a source of nucleophilic hydride, wherein the source of nucleophilic hydride is lithium (sec-butyl)$_3$borohydride; and adding a second compound containing an aldehyde to form the quaternary carbon.

3. The process of claim 2 wherein the compound containing a quaternary carbon is a bryostatin, a peloruside, a mycalamide or an epothilone.

4. The process of claim 2 wherein the compound containing a quaternary is a macrolactone which has the formula

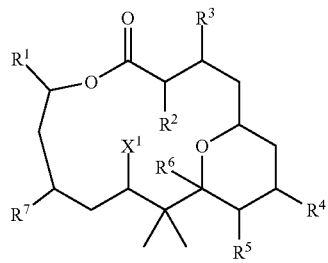

wherein:
R$^1$ is

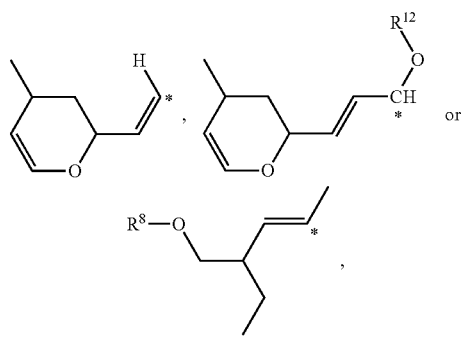

where * shows the point of attachment and R$^8$ and R$^{12}$ are independently hydrogen, alkyl, heteroalkyl, arylalkyl, heteroarylalkyl, or an oxygen protecting group;

R$^2$, R$^3$, R$^4$, R$^5$, R$^6$ and R$^7$ are each independently selected from the group consisting of hydrogen, alkyl, hydroxy, and alkoxy; and X$^1$ is hydrogen, hydroxy, alkoxy or together with the carbon to which it is attached forms a carbonyl or an oxime.

5. The process of claim 4 wherein the macrolactone has the formula

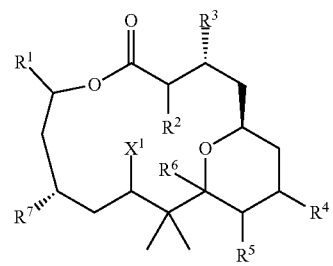

wherein:
R$^1$ is

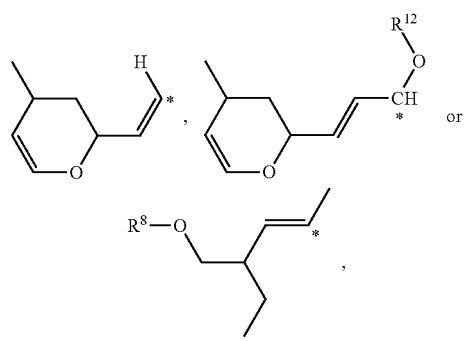

where * shows the point of attachment;

R$^2$, R$^3$, R$^4$, R$^5$, R$^6$ and R$^7$ are each independently selected from the group consisting of hydrogen, alkyl, hydroxy, and alkoxy; X$^1$ is hydrogen, hydroxy, alkyl, alkoxy or together with the carbon to which it is attached forms a carbonyl or an oxime; and R$^8$ and R$^{12}$ are independently hydrogen, alkyl, heteroalkyl, arylalkyl, heteroarylalkyl, or an oxygen protecting group.

6. The process of claim 5 wherein the macrolactone has the formula

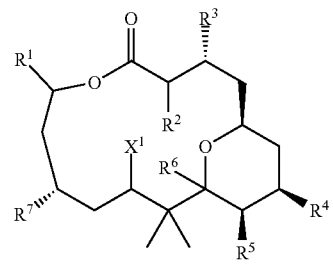

wherein
R$^1$ is

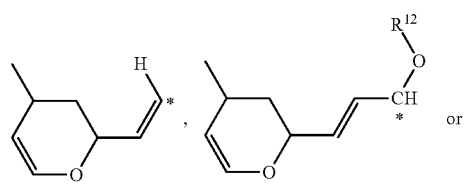

-continued

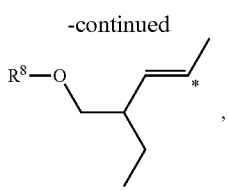

where * shows the point of attachment;
$R^2$, $R^3$, $R^4$, $R^5$, $R^6$ and $R^7$ are each independently selected from the group consisting of hydrogen, alkyl, hydroxy, and alkoxy; $X^1$ is hydrogen, hydroxy, alkyl, alkoxy or together with the carbon to which it is attached forms a carbonyl or an oxime; and
$R^8$ and $R^{12}$ are independently hydrogen, alkyl, heteroalkyl, arylalkyl, heteroarylalkyl, or an oxygen protecting group.

7. The process of claim 6 wherein $R^3$ is methoxy and $R^7$ is methoxy.
8. The process of claim 6 wherein $R^6$ is hydrogen.
9. The process of claim 6 wherein $R^2$ is hydrogen.
10. The process of claim 6 wherein $R^2$ is hydroxy; $R^4$ is methoxy; $R^5$ is hydroxy; $R^6$ is hydroxy; $X^1$ is hydroxy; and $R^1$ is

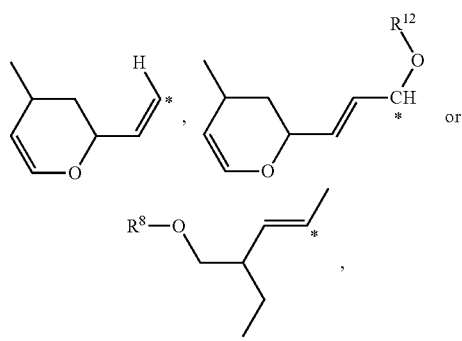

where * shows the point of attachment and $R^8$ and $R^{12}$ are independently hydrogen, alkyl, heteroalkyl, arylalkyl, heteroarylalkyl, or an oxygen protecting group.

11. The process of claim 6 wherein $R^2$ is hydroxy; $R^4$ is methoxy; $R^5$ is hydroxy; $R^6$ is hydrogen, hydroxy, alkyl, or alkoxy; $X^1$ is hydroxy; and $R^1$ is 4-(R)-hydroxymethyl-hex-2-(Z)-ene-2-yl.
12. The process of claim 6 wherein $R^2$ is hydroxy; $R^4$ is methoxy; $R^5$ is hydroxy; $R^6$ is hydroxy; $X^1$ is hydrogen, or epi-hydroxy, alkoxy, or alkyl, or $X^1$ and the attached carbon form a carbonyl; and $R^1$ is 4-(R)-hydroxymethyl-hex-2-(Z)-ene-2-yl.
13. The process of claim 6 wherein $R^2$ is hydrogen, hydroxy, or alkyl; $R^4$ is methoxy; $R^5$ is hydroxy; $R^6$ is hydroxy; $X^1$ is hydroxy; and $R^1$ is 4-(R)-hydroxymethyl-hex-2-(Z)-ene-2-yl.
14. The process of claim 6 wherein $R^2$ is hydroxy; $R^4$ is hydrogen, hydroxy, alkoxy, or alkyl; $R^5$ is hydroxy; $R^6$ is hydroxy; $X^1$ is hydroxy; and $R^1$ is 4-(R)-hydroxymethyl-hex-2-(Z)-ene-2-yl.
15. The process of claim 6 wherein $R^2$ is hydroxy; $R^4$ is methoxy; $R^5$ is hydrogen, hydroxy, alkoxy, or alkyl; $R^6$ is hydroxy; $X^1$ is hydroxy; and $R^1$ is 4-(R)-hydroxymethyl-hex-2-(Z)-ene-2-yl.
16. The process of claim 1 wherein alkyl is $C_1$-$C_4$ alkyl.
17. The process of claim 16 wherein alkyl is methyl.
18. The process of claim 1 wherein a moiety of the following formula

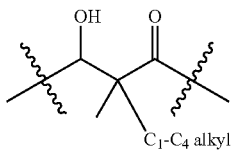

comprises the quaternary carbon formed.
19. The process of claim 1 wherein a moiety of the following formula

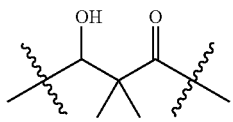 [SMILES: *C(=O)C(C)(C)C(*)O]

comprises the quaternary carbon formed.
20. The process of claim 2 wherein alkyl is $C_1$-$C_4$ alkyl.
21. The process of claim 20 wherein alkyl is methyl.
22. The process of claim 2 wherein a moiety of the following formula

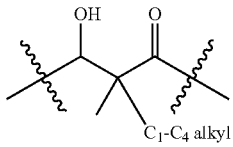

comprises the quaternary carbon formed.
23. The process of claim 2 wherein a moiety of the following formula

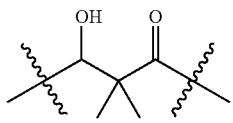 [SMILES: *C(=O)C(C)(C)C(*)O]

comprises the quaternary carbon formed.

* * * * *

UNITED STATES PATENT AND TRADEMARK OFFICE
CERTIFICATE OF CORRECTION

PATENT NO. : 8,580,975 B2
APPLICATION NO. : 12/812067
DATED : November 12, 2013
INVENTOR(S) : Ghosh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 22 days.

Signed and Sealed this
Twenty-second Day of September, 2015

Michelle K. Lee
*Director of the United States Patent and Trademark Office*